(12) United States Patent
Dobson

(10) Patent No.: US 7,691,382 B2
(45) Date of Patent: Apr. 6, 2010

(54) ANTIVIRAL POLYPEPTIDES COMPRISING TANDEM REPEATS OF APOE 141-149 AND VARIANTS THEREOF

(75) Inventor: Curtis Dobson, Manchester (GB)

(73) Assignee: AI2 Limited, Manchester (GB)

( * ) Notice: Subject to any disclaimer, the term of this patent is extended or adjusted under 35 U.S.C. 154(b) by 428 days.

(21) Appl. No.: 10/580,761

(22) PCT Filed: Dec. 17, 2004

(86) PCT No.: PCT/GB2004/005360

§ 371 (c)(1),
(2), (4) Date: May 25, 2006

(87) PCT Pub. No.: WO2005/058959

PCT Pub. Date: Jun. 30, 2005

(65) Prior Publication Data

US 2007/0117746 A1    May 24, 2007

(30) Foreign Application Priority Data

Dec. 17, 2003 (GB) ................... 0329254.7

(51) Int. Cl.
*A61K 39/00* (2006.01)
(52) U.S. Cl. .................................. 424/185.1
(58) Field of Classification Search .............. None
See application file for complete search history.

(56) References Cited

U.S. PATENT DOCUMENTS

2002/0164789 A1 * 11/2002 Laskowitz et al. .......... 435/343

FOREIGN PATENT DOCUMENTS

WO    WO94/04177    3/1994

OTHER PUBLICATIONS

Gait, M. J., and J. Karn, 1995, Progress in anti-HIV structure-based drug design, TIBTECH 13:430-438.*
Hirsch, M. S., et al., 1998, Antiretroviral drug resistance testing in adults with HIV infection, JAMA 279:1984-1991.*
Azuma et al., A Synthetic Peptide Of Human Apoprotein E With Antibacterial Activity, Peptides, (2000), pp. 327-330, 21.
Clay et al., Localization Of A Domain in Apolipoprotein E With Both Cytostatic And Cytotoxic Activity, Biochemistry, (1995), pp. 11142-11151, 34.
Owens et al., Apolipoprotein A-I And Its Amphipathic Helix Peptide Analogues Inhibit Human Immunodeficiency Virus-Induced Syncytium Formation, Journal of Clinical Investigations, (Oct. 1990), pp. 1142-1150, 86.
Srinivas et al., Inhibition Of Virus-Induced Cell Fusion By Apolipoprotein A-I and Its Amphipathic Peptide Analogs, Journal Of Cellular Biochemistry, (1991), pp. 224-237, 45.

* cited by examiner

*Primary Examiner*—Jeffrey Parkin
(74) *Attorney, Agent, or Firm*—Seth D. Levy; Davis Wright Tremaine LLP

(57) ABSTRACT

The present invention concerns polypeptides derived from a tandem repeat of $apoE_{141-149}$ and their uses as medicaments. The peptides may comprise the tandem repeat, and truncations thereof, for which at least one Leucine (L) is replaced by an amino acid with a side chain comprising at least 4 carbon atoms and at least one Nitrogen atom. Such peptides are useful for preventing or treating viral infections.

23 Claims, 10 Drawing Sheets

FIG. 1

Reduction in HSV1 infectivity after treatment with various concentrations of apoE derived peptides

X apoE(141-149)dp

O apoE 263-286

X-axis: Peptide concentration in viral inoculum (μM)
Y-axis: % Infectivity (pfu / well treated / ave pfu per well control x 100)

FIG. 2

Reduction in HSV2 infectivity after treatment with various concentrations of apoE derived peptides

X apoE(141-149)dp

O apoE(263-286)

Reduction in HSV1 infectivity after treatment with various concentrations of apoE derived peptides

FIG. 5

Reduction in HSV1 infectivity after treatment with various concentrations of apoE derived peptides % Infectivity (pfu / well treated / ave pfu per well control x 100) vs. Peptide concentration in viral inoculum (μM)

- + GIN 4
- × GIN 5
- ▲ GIN 6
- ♦ GIN 7

Reduction in HSV1 infectivity after treatment with various concentrations of GIN peptides □ GIN 7
■ GIN 32
▲ GIN 34
✕ GIN 1p

ANTIVIRAL POLYPEPTIDES COMPRISING TANDEM REPEATS OF APOE 141-149 AND VARIANTS THEREOF

This application is the National Phase of International Application PCT/GB2004/005360, filed Dec. 17, 2004, which designated the U.S. and that International Application was published under PCT Article 21(2) in English. This application also includes a claim of priority under 35 U.S.C. §119(a) and §365(b) to British patent application No. GB0329254.7, filed Dec. 17, 2003.

The present invention relates to polypeptides, derivatives or analogues thereof, and to nucleic acids encoding the same with anti-viral activity. The invention further provides the use of such polypeptides, derivatives, analogues or nucleic acids as medicaments, and also in methods of treatment.

Antiviral agents may target one of six stages of the viral replication cycle, these being:
1. Attachment of the virus to the cell;
2. Penetration (or fusion of the viral membrane with the cell membrane);
3. Uncoating of the virus;
4. Replication of the viral nucleic acids;
5. Maturation of progeny virus particles; and
6. Release of progeny virus into extracellular fluids.

Of these six stages, replication (stage 4 above) is the target, which is most effectively influenced by conventional antiviral therapies. Attachment of the virus to the cell is however arguably a more attractive target, as the agent does not need to pass into the host cell. However, this remains an area where few successful therapies have been developed.

It is therefore one object of the present invention to provide therapeutic agents that modulate viral attachment to cells.

Lipoproteins (LPs) are globular macromolecular complexes present in serum and other extracellular fluids, consisting of lipid and protein, and are involved in the transport of lipid around the body. They have been categorised according to their density, with the main classes being high density lipoprotein (HDL), low density lipoprotein (LDL), and very low density lipoprotein (VLDL). Their proteins are referred to as apolipoproteins, and a number of these have been described, including apolipoproteins A, B, C, D, E, F, G, H, and J. In addition, several sub-types of apolipoproteins A, B and C have been documented.

Various interactions have been described linking LPs with viruses. These mostly involving binding of viruses to lipoproteins, with this resulting in either diminished viral infectivity, or conversely providing a 'hitchhiker' method for the virus to enter cells. Additionally, several viruses make use of cellular receptors for LPs (e.g. the LDL receptor) as a means of entering cells, although these receptors can also be released by cells as endogenous antiviral agents (for example a soluble form of the VLDL receptor is released into culture medium by HeLa cells and inhibits human rhinovirus infection). Furthermore, direct binding between certain apolipoproteins and viral proteins has also been reported. For example:
a. Hepatitis C virus core protein binds to apolipoprotein AII;
b. Hepatitis B virus surface antigen binds apolipoprotein H; and
c. Simian immunodeficiency virus (SIV) gp32 protein, and human immunodeficiency virus (HIV) gp41 protein binds to apolipoprotein A1.

Work conducted in the laboratory of the inventor has shown that the presence of latent herpes simplex virus type 1 (HSV1) in brain and the possession of a particular allele of a specific gene—the APOE-e4 allele of the APOE gene—increases the risk of development of Alzheimer's disease (AD). Taken with the additional finding that APOE-e4 carriers are more likely to suffer from cold sores (which are lesions found after reactivation of HSV1 in the peripheral nervous system), these results suggested that APOE-e4 carriers are more likely to suffer damage from HSV1 infections, and suggests that there may be interactions between apolipoprotein E and certain viruses (although such interactions need not necessarily involve antiviral effects). One possible mode of interaction between HSV1 and apoE relates to the independent findings that both of these use cellular heparan sulphate proteoglycan (HSPG) molecules as their initial site of binding to cells, before subsequent attachment to secondary receptors, which raises the possibility that competition may occur at these HSPG sites between HSV1 and apoE containing LPs, which could affect viral entry.

Apolipoprotein E has been shown to have effects on the immune system (seemingly unrelated to its role in lipid metabolism) including suppression of T lymphocyte proliferation. Interactions between a number of peptides derived from residues 130-169 of apoE with lymphocytes have been examined (Clay et al., Biochemistry, 34: 11142-11151 (1995)). The region consisting of apoE residues 141-149 are predicted to be particularly important. Similar interactions of such peptides have been described in neuronal cell lines.

WO 94/04177 discloses that administration of particles containing lipid and amphipathic helical peptides allows clearance of toxins produced by microorganisms, and may increase the effectiveness of antibacterial drugs via an effect on bacterial membranes. However, there is no suggestion that such apoA-derived peptide containing particles may be used as antiviral medicines. It is also not clear whether administration of the peptides in particles, which is a key component of the disclosed development (whether the particles are formed before administration or endogenously), would result in effective utilisation of any antiviral action of either component of the particle.

An amphipathic helical peptide derived from apoA (described by Ananatharamiah in Meth. Enz., 128: 627-647 (1986)) has been shown to prevent fusion of viral membranes with cell membranes, and furthermore prevent the fusion of membranes of infected cells (Srinivas et al. J. Cellular Biochem., 45: 224-237 (1991)). The peptide was also effective at preventing fusion for both HSV1 and HIV (Owens et al., J Clin. Invest., 86: 1142-1150 (1990)). However, the peptide had no effect at all on attachment of HSV I at least to cells (Srinivas et al. supra).

Azuma et al. have reported that peptide derivatives of apoE have a strong antibacterial action, comparable with that of gentamicin (Peptides, 21: 327-330 (2000)). ApoE 133-162 was the most effective, with apoE 134-155 having little effect.

In the light of the research described above, the inventor conducted experiments to evaluate whether or not peptides derived from ApoE (which are capable of forming helices) have antiviral activity. He found that a tandem repeat of a peptide fragment of ApoE, $apoE_{141-149}$ (i.e. 2× LRKL-RKRLL—SEQ ID No.1), did indeed have an antiviral action. While the inventor does not wish to bound by any hypothesis, he believes that this fragment prevents the attachment of virus particles to cells, resulting in a decrease in the infectivity of the virus as measured by a plaque reduction assay technique. Example 1 illustrates how the peptide is effective against viruses such as HSV1, HSV2 and HIV. Accordingly, this peptide may be effective when applied to virus directly, or when applied to virus in the presence of cells, and therefore the peptide can be used to inactivate free virus particles long before they reach their target cells.

In the light of the data generated for a tandem repeat of apoE$_{141-149}$ (i.e. 2× LRKLRKRLL—SEQ ID No.1), the inventors decided to investigate other fragments of apolipoproteins for antiviral activity.

According to a first aspect of the present invention, there is provided a polypeptide, derivative or analogue thereof comprising a tandem repeat of apoE$_{141-149}$ of SEQ ID No 2 or a truncation thereof, characterised in that at least one Leucine (L) residue of SEQ ID No. 2 is replaced by an amino acid with a side chain comprising at least 4 carbon atoms and at least one nitrogen atom.

By "a tandem repeat of apoE$_{141-149}$ of SEQ ID No. 2" we mean the peptide with the amino acid sequence: LRKLRKRLLLRKLRKRLL. The tandem repeat is referred to herein as apoE$_{141-149dp}$ or apoE$_{141-149r}$. This peptide is also assigned the code GIN 1 or GIN1p (wherein p signifies N terminal protection (e.g. by an acetyl group), and C terminal protection (e.g. by an amide group)).

By "a truncation thereof" we mean that the 18 mer of SEQ ID No. 2 is reduced in size by removal of amino acids. The reduction of amino acids may be by removal of residues from the C or N terminal of the peptide or may be by deletion of one or more amino acids from within the core of the peptide (i.e. amino acids 2-17 of SEQ ID No. 2).

By "derivative or analogue thereof" we mean that the amino acids residues are replaced by residues (whether natural amino acids, non-natural amino acids or amino acid mimics) with similar side chains or peptide backbone properties. Additionally the terminals of such peptides may be protected by N and C-terminal protecting groups with similar properties to acetyl or amide groups.

The inventor conducted exhaustive experiments to assess the antiviral activity of peptides from apolipoproteins and derivatives thereof. Peptides and derivatives from ApoE were a particular focus. To the inventors surprise they found that most of the peptides tested had little or no antiviral effect. The surprising exceptions were peptides according to the first aspect of the invention. Examples 2-7 illustrate the efficacy of the peptides according to the invention compared to a tandem repeat of apoE$_{141-149}$ and other peptides derived from apolipoproteins.

The inventor has identified that Tryptophan (W), Arginine (R) or Lysine (K) may be substituted for Leucine in apoE$_{141-149}$ tandem repeats and that such peptides have surprising antiviral activity. The inventor appreciated that these amino acids had side chains comprising at least 4 carbons and also containing a nitrogen atom. Accordingly it is preferred that the amino acid used to replace the leucine is Tryptophan (W), Arginine (R) or Lysine (K) or derivatives thereof in the peptide according to the first aspect of the invention.

The inventor has found that peptides in which at least one L has been substituted with a W have particular antiviral activity. It is therefore most preferred that peptides according to the first aspect of the invention comprise a polypeptide, derivative or analogue thereof comprising a tandem repeat of apoE$_{141-149}$ of SEQ ID No 2 or a truncation thereof, characterised in that at least one Leucine (L) residue of SEQ ID No. 2 is replaced by a Tryptophan (W).

During development work the inventor noted that W substitutions may be expected to increase the likelihood of the peptide forming an alpha helix and wondered if this may explain the antiviral efficacy of compounds according to the first aspect of the invention. However, he does not believe this explains the surprising efficacy of peptides according to the invention. This is because a number of alternative substitutions would be expected to increase alpha helix formation (e.g see Table 1 for calculation of likelihood of various L substituted peptides forming an alpha helix). However the likelihood of forming a helix (table 1) does not correlate with the antiviral activity of peptides according to the present invention (see Example 5).

TABLE 1

Predicted proportion of molecules of various peptides forming alpha-helix in aqueous 0.15M NaCl buffer at 37° C. (%) (using AGADIR secondary structure prediction software available from http://www.embl-heidelberg.de/Services/serrano/agadir/agadir-start.html)

| Amino Acid Substitution | Sequence of peptide | % helix | SEQ ID NO. |
|---|---|---|---|
| E, Glu | ERKERKREEERKERKREE | 6.24 | 26 |
| A, Ala | ARKARKRAAARKARKRAA | 1.85 | 46 |
| D, Asp | DRKDRKRDDDRKDRKRDD | 1.59 | 69 |
| W, Trp | WRKWRKRWWWRKWRKRWW | 1.47 | 3 |
| M, Met | MRKMRKRMMMRKMRKRMM | 1.01 | 47 |
| Y, Tyr | YRKYRKRYYYRKYRKRYY | 0.8 | 6 |
| F, Phe | FRKFRKRFFFRKFRKRFF | 0.79 | 71 |
| I, Ile | IRKIRKRIIIRKIRKRII | 0.6 | 72 |
| Q, Gln | QRKQRKRQQQRKQRKRQQ | 0.55 | 73 |
| No swap | | 0.51 | |

The inventors have also noted:
1. The increase from the W substitution is very small (0.51% of GIN 1p molecules will form a helix, which increases marginally to 1.47% of the W substituted peptide); and
2. A number of other substitutions would be predicted to increase the proportion of molecules forming an alpha helix at any one time. For instance, substituting L for E or A increases the likelihood of forming an alpha-helix beyond that of a W substitution (to 6.24% and 1.87% respectively). However, both of these substitutions in fact abolished antiviral activity (e.g. see peptide GIN39 in Example 3 or Example 5).

Therefore there is no correlation between likelihood of forming an alpha helix, and the strength of antiviral activity for 'L-substituted' peptides according to the invention.

The efficacy of peptides according to the invention is all the more surprising because substitution of L (Leucine) with amino acids according to the first aspect of the invention will make the peptide less amphipathic. (Table 2 illustrates the accepted order of hydrophobicity of amino acids). A skilled person may actually suspect that making a peptide more amphipathic would confer antiviral character. Therefore, unexpectedly, substitutions according to the invention of SEQ ID No. 2 result in a significant increase in their antiviral activity.

TABLE 2

Hydrophobicity of Amino Acids

Phe > Leu = Ile > Tyr = Trp > Val > Met > Pro > Cys > Ala > Gly > Thr > Ser > Lys > Gln > Asn > His > Glu > Asp > Arg

As discussed in more detail below, SEQ ID No 2 may be manipulated according to the first aspect of the invention with a number of different substitutions and deletions to make peptides with antiviral activity. However, it is preferred that the polypeptide according to the first aspect of the invention has at least two W, R or K substitutions, and more preferably three or more W, R or K substitutions.

In addition to one or more L substitutions with W, R or K, it is preferred that at least one further amino acid (preferably at least one further leucine residue) is replaced with Asparagine (N), Tyrosine (Y), Cysteine (C), Methionine (M), Phenylalanine (F), Isoleucine (I), Glutamine (Q) or Histidine (H). It is particularly preferred that such a further substitution is Y or C.

The substituted polypeptide may comprise 18 amino acids (or derivatives thereof) and thereby correspond to the full length of SEQ ID No. 2. However the inventors have surprisingly found that truncated peptides based on SEQ ID No.2 also have efficacy as antiviral agents. Accordingly preferred peptides or derivatives thereof may have less than 18 amino acids. For instance some peptides according to the first aspect of the invention may be 17, 16, 15, 14, 13, 12, 11, 10 or less amino acids in length.

Peptides, and derivatives thereof, according to the present invention preferably have an efficacy for inhibiting viral growth such that their IC50 value is 30 µM or less. It is preferred that the IC50 value is 20 µM or less and more preferred that the IC50 value is 10 µM or less.

Preferred peptides have similar $IC_{50}$ values between viral species. For instance preferred peptides have similar $IC_{50}$ values for inhibiting HSV1, HSV2 and HIV growth.

It will be appreciated that modified amino acids may be substituted into the tandem repeat of $apoE_{141-149}$ with a number of amino acid variants that may be known to those skilled in the art. Such peptides will still have antiviral activity provided that the modification does no significantly alter its chemical characteristics. For instance, hydrogens on the side chain amines of R or K may be replaced with methylene groups (—$NH_2$→—NH(Me) or —$N(Me)_2$).

Preferred peptides according to the first aspect of the invention have the amino acids sequence:

(a) WRKWRKRWWWRKWRKRWW (SEQ ID No. 3). This peptide corresponds to the full length tandem repeat with all Leucines substituted for Tryptophan residues. This peptide is designated GIN 7 when referred to herein.

(b) WRKWRKRWRKWRKR (SEQ ID No. 4). This peptide corresponds to the full length tandem repeat with all Leucines substituted for Tryptophan residues and truncated by the excision of amino acids 9, 10, 17 and 18. This peptide is designated GIN 32 when referred to herein.

(c) WRKWRKRWWLRKLRKRLL (SEQ ID No. 5). This peptide corresponds to the full length tandem repeat with a subset of Leucines substituted for tryptophan residues. This peptide is designated GIN 34 when referred to herein.

(d) WRKWRKRWWRKWRKRWW (SEQ ID No. 52). This peptide corresponds to SEQ ID No. 3 with the W residue at position 9 deleted. This peptide is designated MU 58 when referred to herein.

(e) WRKWRKRWRKWRKRW (SEQ ID No. 53). This peptide corresponds to SEQ ID No. 3 with the W residues at position 9, 10 and 18 deleted. This peptide is designated MU 59 when referred to herein.

(f) WRKWRKRWWFRKWRKRWW (SEQ ID No. 54). This peptide corresponds to SEQ ID No. 3 with the W residue at position 10 substituted with an F. This peptide is designated MU 60 when referred to herein.

(g) WRKWRKRWFFRKWRKRFF (SEQ ID No. 55). This peptide corresponds to SEQ ID No. 3 with the W residues at positions 9, 10, 17 and 18 substituted with F residues. This peptide is designated MU 61 when referred to herein.

(h) WRKCRKRCWWRKCRKRCW (SEQ ID No. 56). This peptide corresponds to SEQ ID No. 3 with the W residues at positions 4, 8, 13 and 17 substituted with C residues. This peptide is designated MU 68 when referred to herein.

(i) LRKLRKRLLWRKWRKRWW (SEQ ID No. 57). This peptide corresponds to SEQ ID No. 2 with the L residues at positions 10, 13, 17 and 18 substituted with W residues. This peptide is designated MU 111 when referred to herein.

(j) LRKLRKRLLLRKLRKRWW (SEQ ID No. 58). This peptide corresponds to SEQ ID No. 2 with the L residues at positions 17 and 18 substituted with W residues. This peptide is designated MU 112 when referred to herein.

(k) LRKLRKRLLWRKWRKRLL (SEQ ID No. 59). This peptide corresponds to SEQ ID No. 2 with the L residues at positions 10 and 13 substituted with W residues. This peptide is designated MU 113 when referred to herein.

(l) WRKWRKRLLLRKLRKRLL (SEQ ID No. 60). This peptide corresponds to SEQ ID No. 2 with the L residues at positions 1 and 4 substituted with W residues. This peptide is designated MU 114 when referred to herein.

(m) WRKLRKRLLLRKLRKRLL (SEQ ID No. 61). This peptide corresponds to SEQ ID No. 2 with the L residue at position 1 substituted with W residues. This peptide is designated MU 115 when referred to herein.

(n) WRKWRKFFFRKWRKRWW (SEQ ID No. 62). This peptide corresponds to SEQ ID No. 3 with the W residues at positions 8, 9 and 10 substituted with F residues and the R residue at position 7 deleted. This peptide is designated MU 116 when referred to herein.

(o) WRKWRKRWWFRKFRKRFF (SEQ ID No. 63). This peptide corresponds to SEQ ID No. 3 with the W residues at positions 10, 13, 17 and 18 substituted with F residues. This peptide is designated MU 117 when referred to herein.

(p) RRKRRKRRRRRKRRKRRR (SEQ ID No. 64). This peptide corresponds to the full length tandem repeat with all Leucines substituted for Arginine (R) residues. This peptide is designated MU 16 when referred to herein.

(q) KRKKRKRKKKRKKRKRKK (SEQ ID No. 65). This peptide corresponds to the full length tandem repeat with all Leucines substituted for Lysine (K) residues. This peptide is designated MU 18 when referred to herein.

The inventor has also appreciated that peptides may be employed according to the invention that comprise more than just a simple dimer tandem repeat of $ApoE_{141-149}$ or a truncation thereof. For instance, peptides comprising a trimer or greater number of repeats may be employed as antiviral agents.

In a further embodiment of the invention, antiviral peptides may be synthesised that comprise a peptide as defined above to which further amino acids have been added. For instance, one, two, three or more amino acids may be added to the C or N terminals of a peptide derived from SEQ ID No. 2. Alternatively the peptide may comprise a tandem repeat of a peptide that is larger than the nine amino acids of SEQ ID No. 1. Such peptides may have amino acids added to the N terminal, C terminal and/or between the $9^{th}$ and $10^{th}$ amino acids of SEQ ID No. 2. It is most preferred that the amino acid is added to C terminal and also between the $9^{th}$ and $10^{th}$ amino acids of SEQ ID No. 2. It will be appreciated that such peptides may then be modified as described above for peptides derived from SEQ ID No. 2. By way of example WRKWRKRWWRKWRKRWWR (SEQ ID No. 66) represents another preferred peptide according to the present invention. This peptide corresponds to the full length tandem repeat of $ApoE_{141-150}$ (i.e. a tandom repeat of LRKLRKRLLR—SEQ ID No. 67) with all Leucines substituted for Tryptophan residues. This peptide is designated MU 83 when referred to herein.

During the development of derivatives of tandem repeats of $apoE_{141-149}$ according to the first aspect of the invention, it was appreciated that truncations of SEQ ID No.2, and variants thereof, also had surprising antiviral activity. These include:

LRKLRKRLLLRKLRK (SEQ ID No. 7). This peptide corresponds to a truncated form of the full length tandem repeat with residues 16, 17 and 18 deleted. This peptide has the advantage that the peptide is shorter than GIN 1 and is therefore cheaper to manufacture. This peptide is designated GIN 4 when referred to herein.

LRKLRKRLRKLRKR (SEQ ID No. 8). This peptide corresponds to the full length tandem repeat truncated by the excision of amino acids 9, 10, 17 and 18. This peptide is designated GIN 8 when referred to herein.

LRKLRKLRKLRKLRKLRK (SEQ ID No. 9). This peptide corresponds to a variation of the full length tandem repeat comprising a repeat of the LRK motif. This peptide is designated GIN 9 when referred to herein.

Furthermore YRKYRKRYYYRKYRKRYY (SEQ ID No. 6) was found to be effect as an antiviral agent. This peptide corresponds to the full length tandem repeat of apoE$_{141-149}$ with all Leucines substituted for Tyrosine residues. This peptide is designated GIN 41 when referred to herein.

According to a second aspect of the invention there is provided a polypeptide, derivative or analogue thereof according to the first aspect of the invention or a peptide of SEQ ID No. 6, 7, 8 or 9 for use as a medicament.

According to a third aspect of the invention there is provided the use of a polypeptide, derivative or analogue thereof according to the first aspect of the invention or a peptide of SEQ ID No. 6, 7, 8 or 9 for the manufacture of a medicament for treating viral infections.

It will be appreciated that the therapeutic effects of polypeptides, derivatives or analogues according to the first aspect of the invention may also be mediated "indirectly" by agents that increase the activity of such polypeptides, derivatives or analogues. The present invention provides the first medical use of such agents.

Thus, according to a fourth aspect of the invention, there is provided an agent capable of increasing the biological activity of a polypeptide, derivative or analogue according to the first aspect of the invention for use as a medicament.

Agents capable of increasing the biological activity of polypeptides, derivatives or analogues according to the invention may achieve their effect by a number of means. For instance, such agents may increase the expression of such polypeptides, derivatives or analogues. Alternatively (or in addition) such agents may increase the half-life of polypeptides, derivatives or analogues according to the invention in a biological system, for example by decreasing turnover of the polypeptides, derivatives or analogues.

Due to their increased biological activity polypeptides, derivatives or analogues according to the first three aspects of the invention are of utility as antiviral agents.

Polypeptides, derivatives or analogues according to the first, second and third aspects of the invention may be used in the treatment of a number of viral infections. The virus may be any virus, and particularly an enveloped virus. Preferred viruses are poxviruses, iridoviruses, togaviruses, or toroviruses. A more preferred virus is a filovirus, arenavirus, bunyavirus, or a rhabdovirus. An even more preferred virus is a paramyxovirus or an orthomyxovirus. It is envisaged that virus may preferably include a hepadnavirus, coronavirus, flavivirus, or a retrovirus. Preferably, the virus includes a herpesvirus or a lentivirus. In preferred embodiments, the virus may be Human Immunodeficiency Virus (HIV), Human herpes simplex virus type 2 (HSV2), or Human herpes simplex virus type 1 (HSV1).

Polypeptides, derivatives or analogues according to the first, second and third aspects of the invention may be used to treat viral infections as a monotherapy (i.e. use of the compound alone) or in combination with other compounds or treatments used in antiviral therapy (e.g. acyclovir, gangcyclovir, ribavirin, interferon, anti-HIV medicaments including nucleoside, nucleotide or non-nucleoside inhibitors of reverse transcriptase, protease inhibitors and fusion inhibitors.)

The polypeptides, derivatives or analogues may be used as a prophylactic (to prevent the development of a viral infection) or may be used to treat existing infections.

Derivatives of polypeptides according to the invention may include derivatives that increase or decrease the polypeptide's half-life in vivo. Examples of derivatives capable of increasing the half-life of polypeptides according to the invention include peptoid derivatives of the polypeptides, D-amino acid derivatives of the polypeptides, and peptide-peptoid hybrids.

Polypeptides according to the invention may be subject to degradation by a number of means (such as protease activity in biological systems). Such degradation may limit the bioavailability of the polypeptides and hence the ability of the polypeptides to achieve their biological function. There are wide ranges of well-established techniques by which peptide derivatives that have enhanced stability in biological contexts can be designed and produced. Such peptide derivatives may have improved bioavailability as a result of increased resistance to protease-mediated degradation. Preferably a peptide derivative or analogue suitable for use according to the invention is more protease-resistant than the peptide from which it is derived. Protease-resistance of a peptide derivative and the peptide from which it is derived may be evaluated by means of well-known protein degradation assays. The relative values of protease resistance for the peptide derivative and peptide may then be compared.

Peptoid derivatives of the peptides of the invention may be readily designed from knowledge of the structure of the peptide according to the first aspect of the invention. Commercially available software may be used to develop peptoid derivatives according to well-established protocols.

Retropeptoids, (in which all amino acids are replaced by peptoid residues in reversed order) are also able to mimic antiviral peptides derived from apolipoproteins. A retropeptoid is expected to bind in the opposite direction in the ligand-binding groove, as compared to a peptide or peptoid-peptide hybrid containing one peptoid residue. As a result, the side chains of the peptoid residues are able point in the same direction as the side chains in the original peptide.

A further embodiment of a modified form of polypeptides according to the invention comprises D-amino acid forms of the polypeptides. The preparation of peptides using D-amino acids rather than L-amino acids greatly decreases any unwanted breakdown of such an agent by normal metabolic processes, decreasing the amounts of agent which need to be administered, along with the frequency of its administration.

The polypeptides, analogues, or derivatives of the invention represent products that may advantageously be expressed by biological cells.

Thus, the present invention also provides, in a fifth aspect, a nucleic acid sequence encoding a polypeptide, derivative or analogue according to the first aspect of the invention.

The nucleic acids encoding apoE$_{141-149}$ has the DNA sequence cttcgtaaacttcgtaaacgtcttctt (SEQ ID. No. 10) whereas GIN 1 has the sequence cttcgtaaacttcgtaaacgtcttct-tcttcgtaaacttcgtaaacgtcttctt (SEQ ID. No. 11).

Preferred nucleic acids according to the fifth aspect of the invention encode the peptides identified herein as GIN 4, 7, 8, 9, 32, 34 and 41 have the following respective sequences:

```
cttcgtaaac ttcgtaaact tcgtaaactt    (SEQ ID No. 16)

cgtaaacttc gtaaacttcg taaa;

tggcgtaaat ggcgtaaacg ttggtggtgg    (SEQ ID No. 12)

cgtaaatggc gtaaacgttg gtgg;

cttcgtaaac ttcgtaaacg tcttcgtaaa    (SEQ ID No. 17)

cttcgtaaac gt;

cttcgtaaac ttcgtaaact tcgtaaactt    (SEQ ID No. 18)

cgtaaacttc gtaaacttcg taaa;

tggcgtaaat ggcgtaaacg ttggcgtaaa    (SEQ ID No. 13)

tggcgtaaac gt;

tggcgtaaat ggcgtaaacg ttggtggctt    (SEQ ID No. 14)

cgtaaacttc gtaaacgtct tctt,;

and tatcgtaaat atcgtaaacg ttattattat    (SEQ ID No. 15)

cgtaaatatc gtaaacgtta ttat.
```

A skilled person will appreciate that the nucleic acid sequence of other preferred peptides according to the present invention may be readily generated.

It will be appreciated that, due to redundancy in the genetic code, a nucleic acid sequence in accordance with the fifth aspect of the invention may vary from the naturally occurring ApoE gene providing a codon encodes a polypeptide, derivative or analogue thereof in accordance with the first aspect of the invention.

It will be appreciated that polypeptides, derivatives and analogues according to the invention represent favourable agents to be administered by techniques involving cellular expression of nucleic acid sequences encoding such molecules. Such methods of cellular expression are particularly suitable for medical use in which the therapeutic effects of the polypeptides, derivatives and analogues are required over a prolonged period.

Thus according to a sixth aspect of the present invention there is provided a nucleic acid sequence according to the fifth aspect of the invention for use as a medicament.

The nucleic acid may preferably be an isolated or purified nucleic acid sequence. The nucleic acid sequence may preferably be a DNA sequence.

The nucleic acid sequence may further comprise elements capable of controlling and/or enhancing its expression. The nucleic acid molecule may be contained within a suitable vector to form a recombinant vector. The vector may for example be a plasmid, cosmid or phage. Such recombinant vectors are highly useful in the delivery systems of the invention for transforming cells with the nucleic acid molecule.

Recombinant vectors may also include other functional elements. For instance, recombinant vectors can be designed such that the vector will autonomously replicate in the cell. In this case elements that induce nucleic acid replication may be required in the recombinant vector. Alternatively, the recombinant vector may be designed such that the vector and recombinant nucleic acid molecule integrates into the genome of a cell. In this case nucleic acid sequences, which favour targeted integration (e.g. by homologous recombination) are desirable. Recombinant vectors may also have DNA coding for genes that may be used as selectable markers in the cloning process.

The recombinant vector may also further comprise a promoter or regulator to control expression of the gene as required.

The nucleic acid molecule may (but not necessarily) be one, which becomes incorporated in the DNA of cells of the subject being treated. Undifferentiated cells may be stably transformed leading to the production of genetically modified daughter cells (in which case regulation of expression in the subject may be required e.g. with specific transcription factors or gene activators). Alternatively, the delivery system may be designed to favour unstable or transient transformation of differentiated cells in the subject being treated. When this is the case, regulation of expression may be less important because expression of the DNA molecule will stop when the transformed cells die or stop expressing the protein (ideally when the required therapeutic effect has been achieved).

The delivery system may provide the nucleic acid molecule to the subject without it being incorporated in a vector. For instance, the nucleic acid molecule may be incorporated within a liposome or virus particle. Alternatively a "naked" nucleic acid molecule may be inserted into a subject's cells by a suitable means e.g. direct endocytotic uptake.

The nucleic acid molecule may be transferred to the cells of a subject to be treated by transfection, infection, microinjection, cell fusion, protoplast fusion or ballistic bombardment. For example, transfer may be by ballistic transfection with coated gold particles, liposomes containing the nucleic acid molecule, viral vectors (e.g. adenovirus) and means of providing direct nucleic acid uptake (e.g. endocytosis) by application of the nucleic acid molecule directly.

It will be appreciated that the polypeptides, agents, nucleic acids or derivatives according to the present invention may be used in a monotherapy (i.e. use of polypeptides, agents, nucleic acids or derivatives according to the invention alone to prevent and/or treat a viral infection). Alternatively, polypeptides, agents, nucleic acids or derivatives according to the invention may be used as an adjunct, or in combination with, known therapies.

Polypeptides, agents, nucleic acids or derivatives according to the invention may be combined in compositions having a number of different forms depending, in particular on the manner in which the composition is to be used. Thus, for example, the composition may be in the form of a powder, tablet, capsule, liquid, ointment, cream, gel, hydrogel, aerosol, spray, micelle, transdermal patch, liposome or any other suitable form that may be administered to a person or animal. It will be appreciated that the vehicle of the composition of the invention should be one which is well tolerated by the subject to whom it is given, and is preferably adapted to enable delivery of the polypeptides, agents, nucleic acids or derivatives to the target tissue.

Compositions comprising polypeptides, agents, nucleic acids or derivatives according to the invention may be used in a number of ways. For instance, oral administration may be required in which case the compound may be contained within a composition that may, for example, be ingested orally in the form of a tablet, capsule or liquid. Alternatively the composition may be administered by injection into the blood stream. Injections may be intravenous (bolus or infusion) or subcutaneous (bolus or infusion). The compounds may be administered by inhalation (e.g. intranasally).

Compositions may be formulated for topical use. For instance, ointments may be applied to the skin, areas in and around the mouth or genitals to treat specific viral infections.

Topical application to the skin is particularly useful for treating viral infections of the skin or as a means of transdermal delivery to other tissues. Intravaginal administration is effective for treating sexually transmitted diseases (including AIDS).

Polypeptides, agents, nucleic acids or derivatives may also be incorporated within a slow or delayed release device. Such devices may, for example, be inserted on or under the skin, and the compound may be released over weeks or even months. Such devices may be particularly advantageous when long term treatment with a polypeptide, agent, nucleic acid or derivative according to the invention is required and which would normally require frequent administration (e.g. at least daily injection).

It will be appreciated that the amount of a polypeptide, agent, nucleic acid or derivative that is required is determined by its biological activity and bioavailability which in turn depends on the mode of administration, the physicochemical properties of the polypeptide, agent, nucleic acid or derivative employed and whether the polypeptide, agent, nucleic acid or derivative is being used as a monotherapy or in a combined therapy. The frequency of administration will also be influenced by the above-mentioned factors and particularly the half-life of the polypeptide, agent, nucleic acid or derivative within the subject being treated.

Optimal dosages to be administered may be determined by those skilled in the art, and will vary with the particular polypeptide, agent, nucleic acid or derivative in use, the strength of the preparation, the mode of administration, and the advancement of the disease condition. Additional factors depending on the particular subject being treated will result in a need to adjust dosages, including subject age, weight, gender, diet, and time of administration.

It will be appreciated that a skilled person will be able to calculate required doses, and optimal concentrations of the peptides at a target tissue, based upon the pharmacokinetics of the peptides and in particular the $IC_{50}$ values given in the Examples.

Generally, a daily dose of between 0.01 μg/kg of body weight and 0.5 g/kg of body weight of polypeptides, agents, nucleic acids or derivatives according to the invention may be used for the prevention and/or treatment of a viral infection, depending upon which specific polypeptide, agent, nucleic acid or derivative is used. More preferably, the daily dose is between 0.01 mg/kg of body weight and 200 mg/kg of body weight, and most preferably, between approximately 1 mg/kg and 100 mg/kg.

Known procedures, such as those conventionally employed by the pharmaceutical industry (e.g. in vivo experimentation, clinical trials, etc.), may be used to establish specific formulations of polypeptides, agents, nucleic acids or derivatives according to the invention and precise therapeutic regimes (such as daily doses of the polypeptides, agents, nucleic acids or derivatives and the frequency of administration).

Daily doses may be given as a single administration (e.g. a single daily injection). Alternatively, the polypeptide, agent, nucleic acid or derivative used may require administration twice or more times during a day. As an example, polypeptides, agents, nucleic acids or derivatives according to the invention may be administered as two (or more depending upon the severity of the condition) daily doses of between 25 mg and 7000 mg (i.e. assuming a body weight of 70 kg). A patient receiving treatment may take a first dose upon waking and then a second dose in the evening (if on a two dose regime) or at 3 or 4 hourly intervals thereafter. Alternatively, a slow release device may be used to provide optimal doses to a patient without the need to administer repeated doses.

This invention provides a pharmaceutical composition comprising a therapeutically effective amount of a polypeptide, agent, nucleic acid or derivative according to the invention and optionally a pharmaceutically acceptable vehicle. In one embodiment, the amount of the polypeptide, agent, nucleic acid or derivative is an amount from about 0.01 mg to about 800 mg. In another embodiment, the amount of the polypeptide, agent, nucleic acid or derivative is an amount from about 0.01 mg to about 500 mg. In another embodiment, the amount of the polypeptide, agent, nucleic acid or derivative is an amount from about 0.01 mg to about 250 mg. In another embodiment, the amount of the polypeptide, agent, nucleic acid or derivative is an amount from about 0.1 mg to about 60 mg. In another embodiment, the amount of the polypeptide, agent, nucleic acid or derivative is an amount from about 0.1 mg to about 20 mg.

This invention provides a process for making a pharmaceutical composition comprising combining a therapeutically effective amount of a polypeptide, agent, nucleic acid or derivative according to the invention and a pharmaceutically acceptable vehicle. A "therapeutically effective amount" is any amount of a polypeptide, agent, nucleic acid or derivative according to the first aspect of the invention which, when administered to a subject provides prevention and/or treatment of a viral infection. A "subject" is a vertebrate, mammal, domestic animal or human being.

A "pharmaceutically acceptable vehicle" as referred to herein is any physiological vehicle known to those of ordinary skill in the art useful in formulating pharmaceutical compositions.

In a preferred embodiment, the pharmaceutical vehicle is a liquid and the pharmaceutical composition is in the form of a solution. In another embodiment, the pharmaceutically acceptable vehicle is a solid and the composition is in the form of a powder or tablet. In a further embodiment, the pharmaceutical vehicle is a gel and the composition is in the form of a cream or the like.

A solid vehicle can include one or more substances which may also act as flavouring agents, lubricants, solubilisers, suspending agents, fillers, glidants, compression aids, binders or tablet-disintegrating agents; it can also be an encapsulating material. In powders, the vehicle is a finely divided solid that is in admixture with the finely divided active polypeptide, agent, nucleic acid or derivative. In tablets, the active polypeptide, agent, nucleic acid or derivative is mixed with a vehicle having the necessary compression properties in suitable proportions and compacted in the shape and size desired. The powders and tablets preferably contain up to 99% of the active polypeptide, agent, nucleic acid or derivative. Suitable solid vehicles include, for example, calcium phosphate, magnesium stearate, talc, sugars, lactose, dextrin, starch, gelatin, cellulose, polyvinylpyrrolidine, low melting waxes and ion exchange resins.

Liquid vehicles are used in preparing solutions, suspensions, emulsions, syrups, elixirs and pressurized compositions. The active polypeptide, agent, nucleic acid or derivative can be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal, intravenous and particularly subcutaneous, intracerebral or intracerebroventricular injection. The polypeptide, agent, nucleic acid or derivative may be prepared as a sterile solid composition that may be dissolved or suspended at the time of administration using sterile water, saline, or other appropriate sterile injectable medium. Vehicles are intended to include necessary and inert binders, suspending agents, lubricants, flavourants, sweeteners, preservatives, dyes, and coatings.

Polypeptides, agents, nucleic acids or derivatives according to the invention can be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like.

Polypeptides, agents, nucleic acids or derivatives according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

The invention will be further described, by way of example only, with reference to the following Examples and figures in which:

FIG. 1 shows the effect of apoE141-149dp and apoE$_{263-286}$ on HSV1 infectivity. (points are derived from the average of up to four values) as described in Example 1;

FIG. 2 shows the effect of apoE$_{141-149dp}$ or apoE$_{263-286}$ on HSV2 infectivity (points are derived from the average of up to four values) as described in Example 1;

FIG. 5 illustrates the effect of 4 peptides (GIN 4-7) on HSV1 infectivity as described in Example 2;

Figure 7:
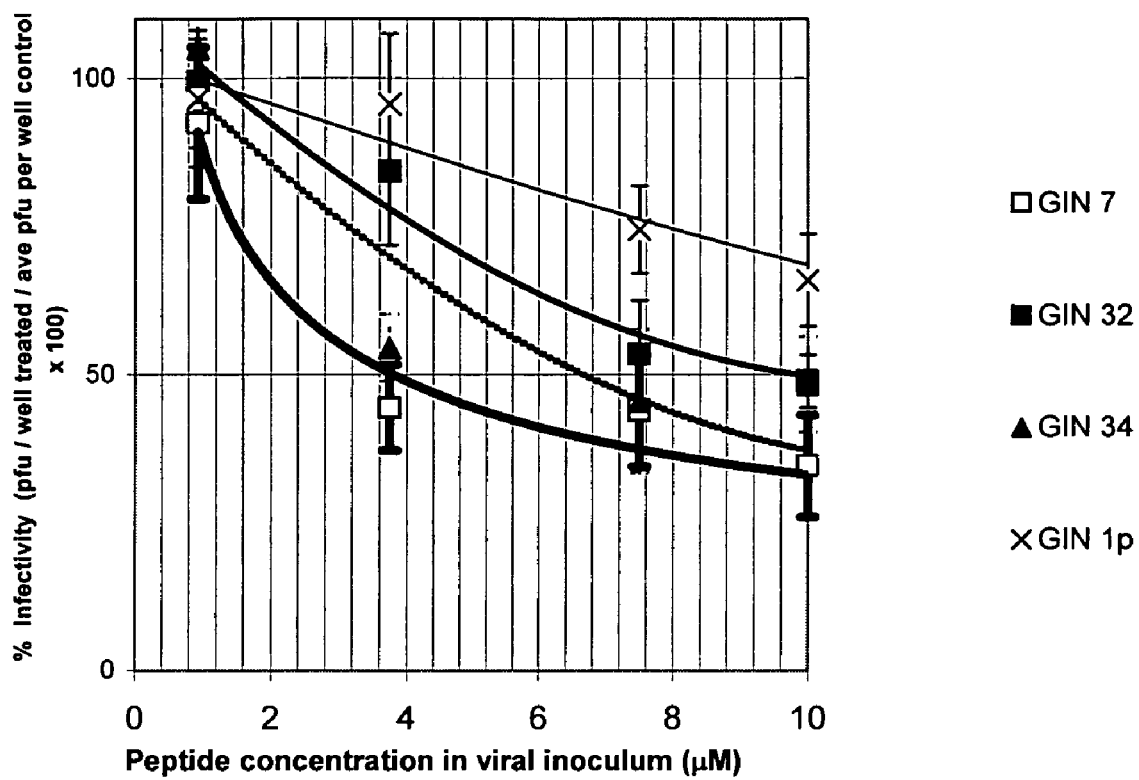
Figure 8:
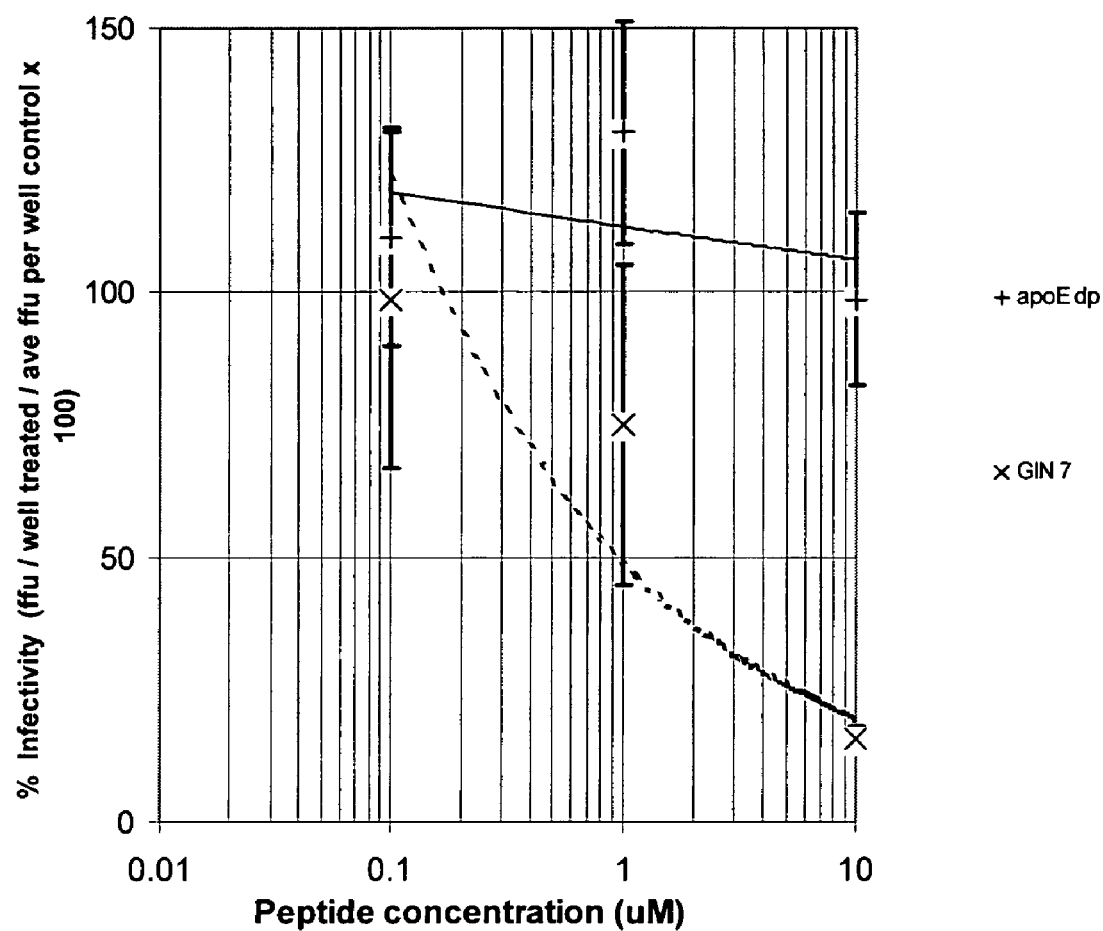
Figure 9:
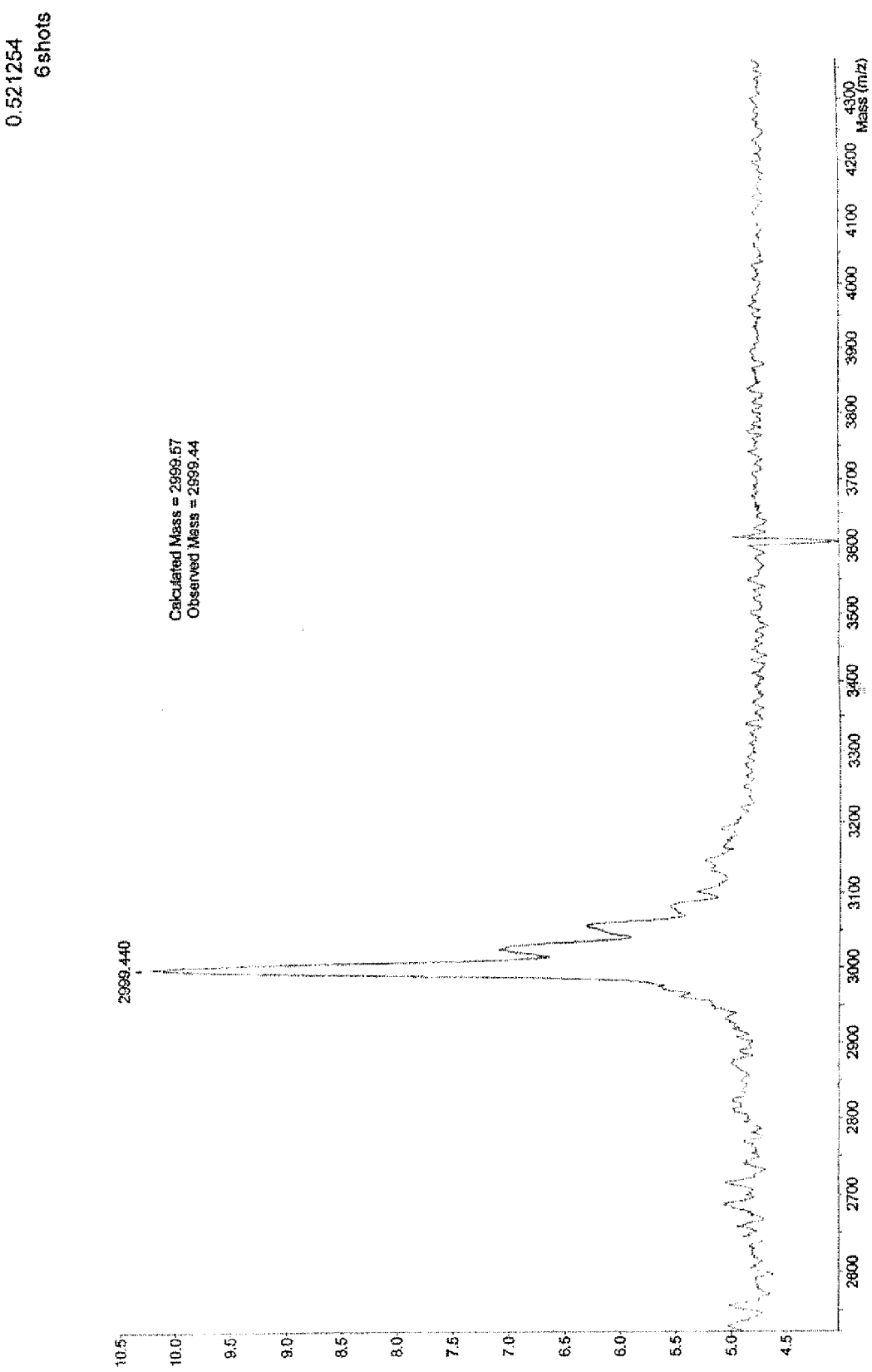
Figure 10:
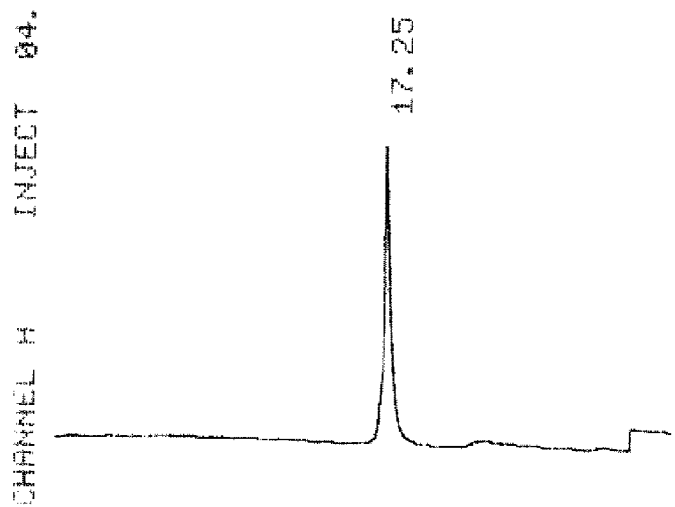

FIG. 7 compares and illustrates the effect of peptides GIN 7, GIN 32, GIN 34, and GIN 1p on HSV1 infectivity as described in Example 2;

FIG. 8 illustrates the anti-HIV action of peptide GIN7 against HIV isolate SF162, grown in NP-2 glioma cells overexpressing CCR5 co-receptors as described in Example 4;

FIG. 9 shows typical mass spectrometry data for GIN7 and illustrates that the peptide was >95% purity;

FIG. 10 shows typical HPLC data for GIN7 and illustrates that the peptide was >95% purity.

EXAMPLE 1

Experiments were conducted with ApoE$_{141-149}$ to establish whether or not the peptide had any efficacy as an antiviral agent.

1.1 HSV1

FIG. 1 and table 1 show typical results for the test for anti-HSV1 activity. The assay involved treating confluent Vero cells in 24-well plates with medium containing virus and varying amounts of peptide for one hour, followed by removal of this inoculum, and addition of viscous 'overlay' medium, containing 0.2% high viscosity carboxymethylcellulose. The overlay medium only allows infection of those cells immediately adjacent to an infected cell. After 2 days incubation and then fixation and staining, small patches of infected cells (or 'plaques') are visible, which are counted. Each of these corresponds to the infection of a single cell during the one hour inoculation. ApoE$_{141-149dp}$ produced a 40% reduction in plaque number at a concentration of around 20 μM. Note the peptide was only present in the experimental system for 1 hour.

TABLE 1

HSV1 plaque formation in Vero cells after inoculation with virus containing either apoE$_{141-149dp}$ or apoE$_{263-286}$. Values for untreated wells are underlined.

| [μM] | ApoE$_{141-149dp}$ | | | | | ApoE$_{263-286}$ | | | | |
|---|---|---|---|---|---|---|---|---|---|---|
| | 1 | 2 | 3 | 4 | Mean ± sd | 1 | 2 | 3 | 4 | Mean ± sd |
| <u>0</u> | <u>96</u> | <u>102</u> | <u>123</u> | | <u>107 ± 14.2</u> | | | | | |
| 5 | 129 | 106 | 103 | 100 | 110 ± 13.2 | 113 | 119 | 122 | 126 | 120 ± 5.5 |
| 10 | 73 | 87 | 76 | 89 | 81 ± 7.9 | 116 | 124 | 102 | | 114 ± 11.1 |
| 20 | 68 | 67 | 63 | 63 | 65 ± 2.6 | 148 | 112 | 133 | 114 | 127 ± 17.0 |
| 30 | 72 | 71 | 56 | | 66 ± 9.0 | 134 | 109 | 114 | 125 | 121 ± 11.2 |
| 40 | 64 | 65 | 53 | 68 | 63 ± 6.6 | 120 | 113 | 125 | 144 | 126 ± 11.2 |

1.2 HSV2

FIG. 2 and table 2 show typical results for the test for anti-HSV2 activity. The assay was carried out as for the anti-HSV1 assay, except Hep-2 cells were used rather than Vero cells. ApoE$_{141\text{-}149dp}$ produced a 50% reduction in plaque number at a concentration of around 20 μM. Again note that the peptide was only present in the experimental system for 1 hour.

EXAMPLE 2

Given the knowledge gained by the inventors following the work reported in Example 1, experiments were conducted to evaluate the antiviral effects of a large number of peptides derived from apolipoproteins. Surprisingly, the inventors found that only a minority of the peptides tested had antiviral effects (see 2.2). Such peptides represent peptides according to the invention.

TABLE 2

HSV2 plaque formation in HEp-2 cells after inoculation with virus containing either apoE$_{141\text{-}149dp}$ or apoE$_{263\text{-}286}$. Values for untreated wells are underlined.

| | ApoE$_{141\text{-}149dp}$ | | | | | ApoE$_{263\text{-}286}$ | | | | |
|---|---|---|---|---|---|---|---|---|---|---|
| [μM] | 1 | 2 | 3 | 4 | Mean ± sd | 1 | 2 | 3 | 4 | Mean ± sd |
| 0 | <u>156</u> | <u>137</u> | <u>162</u> | <u>152</u> | 152 ± 10.7 | | | | | |
| 5 | 160 | 134 | 140 | 130 | 141 ± 13.3 | 135 | 160 | 161 | 152 | 152 ± 12.0 |
| 10 | 125 | 113 | 131 | 132 | 125 ± 8.7 | 157 | 121 | 151 | 134 | 141 ± 16.1 |
| 20 | 82 | 72 | 73 | 81 | 77 ± 5.2 | 118 | 150 | 182 | 134 | 146 ± 27.3 |
| 30 | 76 | 77 | 71 | 72 | 74 ± 2.9 | 118 | 117 | 103 | 159 | 124 ± 24.2 |
| 40 | 51 | 59 | 69 | 49 | 57 ± 9.1 | 132 | 144 | 125 | 124 | 131 ± 24.2 |

1.3 HIV

Figure 3:
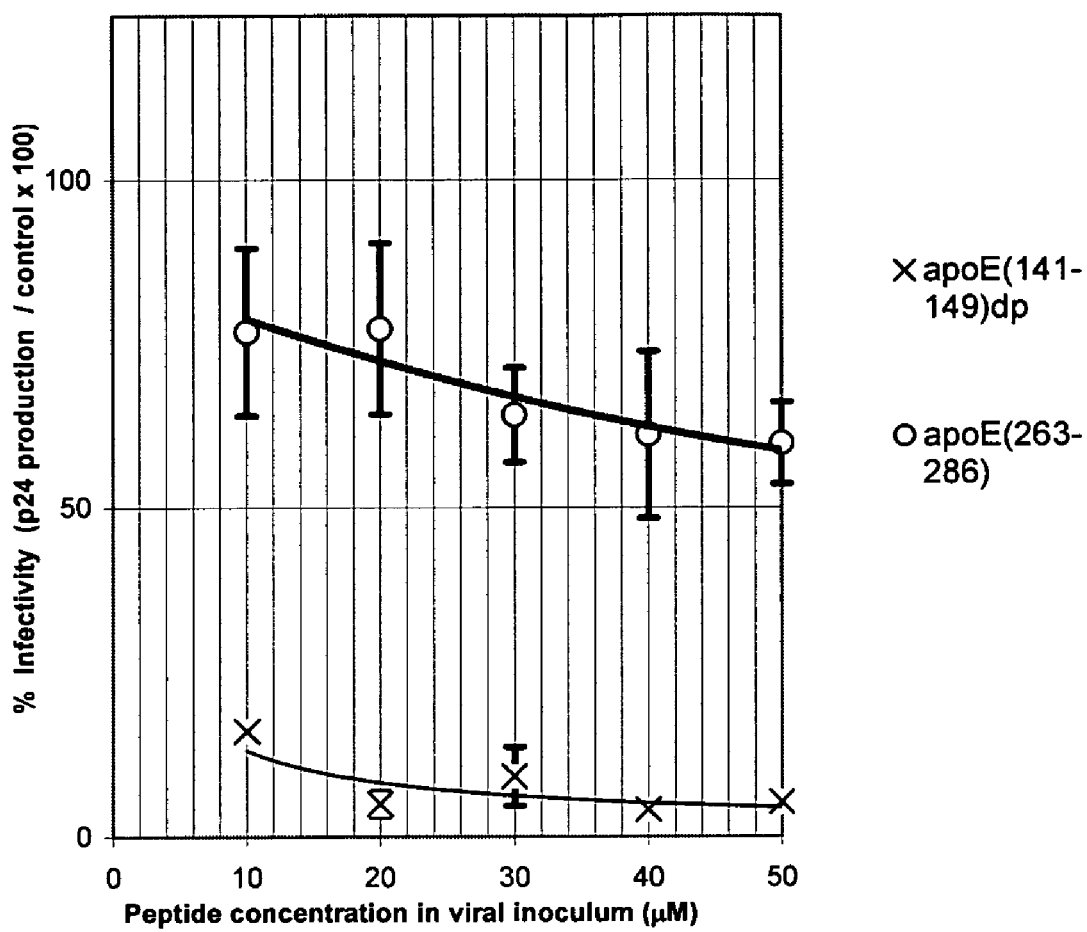
FIG. 3 illustrates inhibition of HIV-1 p24 production, as measured by ELISA, by apoE$_{141-149r}$, and apoE$_{263-286}$ in acutely infected U937 cells (values are the average of three experiments) as described in Example 1 (ApoE$_{141-149dp}$ was significantly active against HIV (ANOVA, p<0.001), whereas the activity of apoE$_{263-286}$ against HIV did not reach significance (ANOVA; 0.06<p<0.62))

FIG. 3 and table 3 show typical results for the test for anti-HIV activity. The assay was carried out by incubating HIV infected U937 cells in the presence of various levels of peptide for 7 days, followed by assay for levels of the HIV protein p24 in the cells using an Enzyme Linked Immunoabsorbant Assay (ELISA) technique. ApoE$_{141\text{-}149dp}$ produced a 95% reduction in infectivity at 20 μM. ApoE$_{263\text{-}286}$ produced a 20% reduction in infectivity at 20 μM, which did not reach statistical significance.

The effect on HIV appears at lower peptide concentrations, though this may be due to peptide being in contact with cells for 7 days, as opposed to just 1 hour in plaque reduction assays with herpes viruses.

2.1 Materials and Methods 2.1.1 Cell culture.

African Green Monkey Kidney (Vero) cells were maintained in Eagle's minimum essential medium with Earle's salt (EMEM) and supplemented with 10% foetal calf serum (heat-inactivated), 4 mM L-glutamine, and 1% (v/v) nonessential amino acids, plus penicillin and streptomycin (100 IU/mg and 100 mg/ml, respectively) (maintenance medium referred to as 10% EMEM). The cells were incubated at 37° C. in a humidified atmosphere of air with 5% CO$_2$.

On harvesting, monolayers were washed in phosphate-buffered saline (PBS), and dislodged by incubating with

TABLE 3

Inhibition of HIV-1 p24 production, as measured by ELISA, by apoE$_{141\text{-}149dp}$ and apoE$_{263\text{-}286}$ in acutely infected U937 cells.

| | % Decrease in HIV p24 Production | | | | | | | |
|---|---|---|---|---|---|---|---|---|
| | ApoE$_{141\text{-}149dp}$ | | | | ApoE$_{263\text{-}286}$ | | | |
| [μM] | Exp. 1 | Exp. 2 | Exp. 3 | Mean ± sd | Exp. 1 | Exp. 2 | Exp. 3 | Mean ± sd |
| 0 | 0 | 0 | 0 | 0 | 0 | 0 | 0 | 0 |
| 10 | 91.66 | 70.31 | 89.85 | 83.94 ± 11.84 | 31.75 | 8.50 | 29.38 | 23.21 ± 12.79 |
| 20 | 96.87 | 95.08 | 93.10 | 95.02 ± 1.89 | 7.69 | 29.71 | 30.91 | 22.77 ± 13.07 |
| 30 | 95.94 | 88.63 | 87.77 | 90.78 ± 4.49 | 37.94 | 27.83 | 41.78 | 35.85 ± 7.21 |
| 40 | 96.80 | 95.47 | 95.33 | 95.87 ± 0.81 | 23.50 | 30.08 | 48.04 | 38.87 ± 12.70 |
| 50 | 95.73 | 93.25 | 95.38 | 94.79 ± 1.34 | 33.36 | 41.45 | 45.66 | 40.16 ± 6.25 |

The results presented in 1.1-1.3 illustrate that Apo E$_{141\text{-}149dp}$ was more efficacious than ApoE$_{263\text{-}286}$.

In the light of these results, the inventors proceeded to test other peptides generated from apolipoproteins to investigate whether or not such peptides had antiviral activity (see Example 2).

trypsin in PBS for 30 min, before inactivating trypsin by addition of an equal volume of 10% EMEM and centrifuging at 500 g (5 min, 4° C.). Cell pellets were resuspended in 10% EMEM, prior to cell counting and seeding of 24-well plates. For antiviral assays, medium containing only 0.5% FCS was used (referred to as 0.5% EMEM).

2.1.2 Virus

Three separate passages of HSV1 virus were prepared by infecting Vero cells, and preparing semi-pure suspensions of virus from tissue culture supernatant and cell lysates, before freezing aliquots of virus at −85° C. Viral infectivity was assessed by carrying out plaque assays on serial dilutions of thawed aliquots (expressed in pfu/ml).

2.1.3 Peptides

Peptides were obtained in lyophilised form from a commercial supplier (AltaBioscience, University of Birmingham or Advanced Biomedical), and were produced at 5 micromole scale. N-terminals were protected by addition of an acetyl group, and the C-terminals were protected by addition of an amide group.

Molecular weight of peptides was confirmed by laser desorption mass spectrometry using a Finnigan LASERMAT 2000 MALDI-time of flight mass analyzer or a Scientific Analysis Group MALDI-TOF mass spectrometer. HPLC purification of peptides was performed using a Vydac analytical C-4 reverse phase column, using 0.1% TFA and 0.1% TFA/80% acetonitrile as solvents, or for some peptides an ACE C18 Reverse Phase column, using 0.05% TFA and 60% acetonitrile as solvents. Typical mass spectrometry data and high performance liquid chromatography (HPLC) traces (purity >95%) for peptide GIN 7 (SEQ ID No. 3) are shown in FIGS. 9 and 10.

Small quantities of peptide were weighed in sterile Eppendorf tubes, before addition of sufficient 0.5% EMEM to produce a 1.5 mM stock solution, which was frozen at −20° C. in aliquots.

2.1.4 Plaque Reduction Assays.

Vero cells were seeded at 125,000 cells per well in 10% EMEM, and were incubated overnight resulting in confluent monolayers. Peptides were diluted in 0.5% EMEM to give 2× final desired concentration, and 100 µl aliquots were arranged on 96-well plates in arrangement to be used for 24-well plate; control wells containing normal 0.5% EMEM were also prepared. Virus stocks (p3) were thawed, and diluted in 0.5% EMEM such that there were around 100 pfu in 100 µl. Each 24-well plate was inoculated separately. Firstly 100 µl of virus stock was added to the peptide or control medium arranged on a 96-well plate. This was incubated at 37° C. for ten minutes before inoculation. Medium was removed from four wells of a 24-well plate containing confluent Vero, and the 200 µl inoculum added to the appropriate well. Once all wells were treated, the 24-well plate was incubated for a further 60-80 minutes. Finally the peptide-containing inoculum was removed, and 1 ml of 1% EMEM containing 1% carboxymethylcellulose was added to each well. Plates were incubated for a further 22 hours or in some experiments 40 hours, before removal of overlay, and addition of 10% formaldehyde in PBS. After a further one hour incubation, fixative was removed, monolayers washed several times with tap water, and stained with carbol fuchsin solubilised in water. After 30 minutes stain was removed, and plates washed several times with tap water, before being air dried. Plaques were counted using an Olympus IX70 Inverting Microscope, and antiviral effect expressed as a percentage of the control value for each peptide concentration. The IC50 was calculated from plots of inhibitory effect against peptide concentration.

2.1.5 Toxicity Testing.

Vero cells were seeded in 96-well plates at 30,000 cells per well in 10% EMEM, and were incubated overnight resulting in confluent monolayers. GIN peptides were diluted in 0.5% EMEM to give final desired concentration, and 100 µl aliquots were arranged on separate non-cell containing 96-well plates, prior to taking Vero 96-well plates, removing 10% EMEM, and adding 0.5% EMEM containing peptides. After incubating for 48 hours, 25 µl of 1.5 mg/ml MTT solution (in 0.5% EMEM) was added per well, and plates returned to incubator for one hour. Finally, medium was removed from wells, and blue formazan crystals solubilised by addition of 100 µl of dimethylsulphoxide (DMSO). Absorbance of resulting solutions was then measured at 570 nm, and toxic effect expressed as a percentage of the control value for each peptide concentration. Where possible, the EC50 was calculated from plots of toxic effect against peptide concentration. Fortunately, no evidence of toxicity was found for the cell line tested, using peptide at 40 µM exposed to cells for 2 days.

2.2 Results

Table 4 summarises data obtained for 16 peptides identified as GIN 1, GIN 1p and GIN 2-15.

TABLE 4

| Peptide | SEQ ID No. | Apparent IC50 (µM) | Sequence | Size |
|---------|------------|--------------------|----------|------|
| GIN 1   | 2          | 16.5               | LRKLRKRLLLRKLRKRLL | 18 |
| GIN 1p  | 2          | 10                 | LRKLRKRLLLRKLRKRLL | 18 |
| GIN 2   | 24         | >40                | LRKRLLLRKLRKRLL | 15 |
| GIN 3   | 31         | No Activity        | RLLLRKLRKRLL | 12 |
| GIN 4   | 7          | 29.5               | LRKLRKRLLLRKLRK | 15 |
| GIN 5   | 25         | >40                | LRKLRKRLLLRK | 12 |
| GIN 6   | 26         | >40                | ERKERKREEERKERKREE | 18 |
| GIN 7   | 3          | <5                 | WRKWRKRWWWRKWRKRWW | 18 |
| GIN 8   | 8          | 13                 | LRKLRKRLRKLRKR | 14 |
| GIN 9   | 9          | 15.5               | LRKLRKLRKLRKLRKLRK | 18 |
| GIN 10  | 22         | 39                 | RLLRLLLRLLRLLRLLRLL | 18 |
| GIN 11  | 20         | 36.5               | QSTEELRVRLASHLRKLRKRLL | 22 |
| GIN 12  | 27         | >40                | LRKLRKRLLR DADDLQKRLA | 20 |
| GIN 13  | 28         | >40                | RDADDLQKR RDADDLQKR | 20 |
| GIN 14  | 29         | >40                | GERLRARMEGERLRARME | 18 |
| GIN 15  | 30         | >40                | RLRARMEEMRLRARMEEM | 18 |

Figure 4:
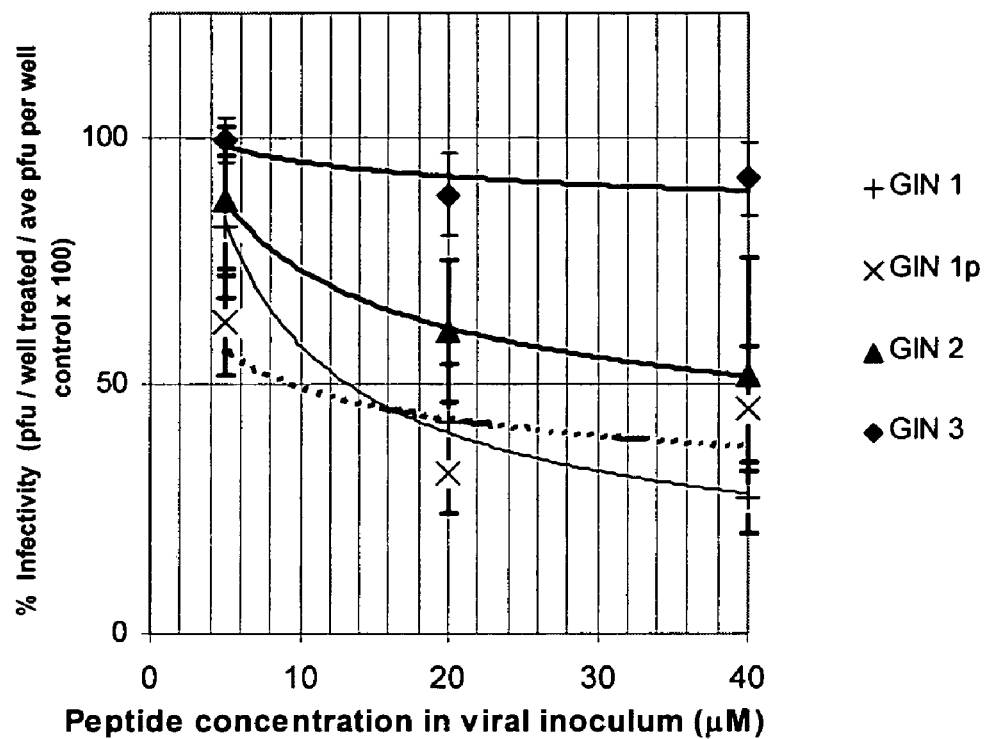
FIG. 4 illustrates the effect of 4 peptides (GIN1, 1p, 2 and 3) on HSV1 infectivity as described in Example 2.

FIG. 4 illustrates that the ApoE$_{141-149dp}$ (labelled as GIN 1) had good efficacy for reducing HSV1 infectivity. A related peptide GIN 1p (GIN 1 with N and C terminal protection) had similar efficacy.

As illustrated in Table 4 the inventors tested a number of other related peptides (identified as GIN 2, GIN 3, GIN 4, GIN 5, GIN 6, GIN 10, GIN 11, GIN 12, GIN 13, GIN 14 and GIN 15) and it was found that they had no, or poor, efficacy for reducing viral infectivity.

In addition, the inventor found to his surprise, that a subset of the tested peptides (which are peptides according to the present invention) were effective as antiviral agents. FIG. 5 illustrates that the peptide designated GIN 7 had efficacy for reducing HSV-1 infectivity.

Figure 6:
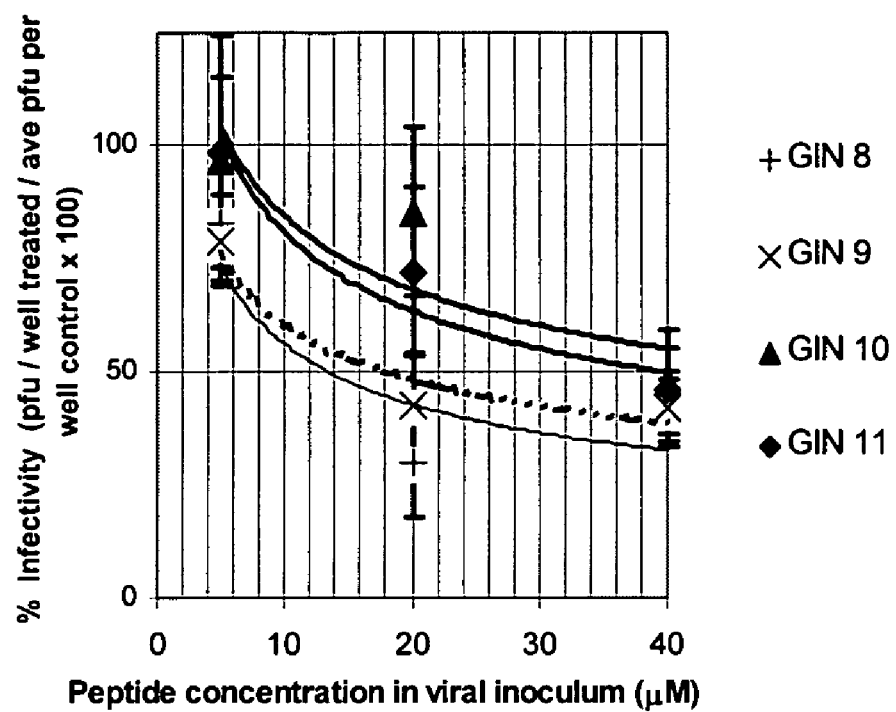
FIG. 6 illustrates the effect of 4 peptides (GIN 8-11) on HSV1 infectivity as described in Example 2.

FIG. 6 illustrates that the peptides designated GIN 8 and GIN 9 also had efficacy for reducing HSV-1 infectivity.

Table 5 and FIG. 4a illustrate that a number of peptides related or similar to the ApoE$_{141-149dp}$ peptide (identified as peptides GIN 17-31 in Table 4a) had no, or poor, efficacy for reducing viral infectivity. The inventors had rationally designed these molecules in the expectation that they may have anti-HSV1 activity and, based on the data presented in Table 4, a skilled person may have expected such peptides to have similar efficacy to those claimed according to the invention. The fact that these peptides had little effect makes the usefulness of the claimed peptides all the more surprising.

TABLE 5

| Peptide | SEQ ID No. | Apparent IC50 (μM) | Sequence | Size |
|---|---|---|---|---|
| GIN 17 | 33 | NA | RALVDTLKFVTQAEGAK | 17 |
| GIN 18 | 34 | NA | PYLDDFQKKWQEEMELYRQKVE | 22 |
| GIN 19 | 35 | NA | PLGEEMRDRARAHVDALRTHLA | 22 |
| GIN 20 | 36 | NA | PYSDELRQRLAARLEALKENGG | 22 |
| GIN 21 | 37 | NA | ARLAEYHAKATEHLSTLSEKAK | 22 |
| GIN 22 | 19 | 36 | DWLKAFYDKVAEKLKEAF | 18 |
| GIN 23 | 38 | NA | PVLDEFREKLNEELEALKQKMK | 22 |
| GIN 24 | 39 | NA | VTDYGKDLMEKVKSPELQ | 18 |
| GIN 25 | 40 | NA | VTDYGKDLMEKVKEWLNS | 18 |
| GIN 26 | 41 | NA | NFHAMFQPFLEMIHEAQQ | 28 |
| GIN 27 | 42 | NA | CKNKEKKCCKNKEKKC | 18 |
| GIN 28 | 43 | NA | LRKEKKRLLLRKEKKRLL | 18 |
| GIN 29 | 21 | 38.5 | HMLDVMQDHFSRASSIIDEL | 20 |
| GIN 30 | 44 | NA | LQVAERLTRKYNELLKSYQ | 19 |
| GIN 31 | 45 | NA | KFMETVAEKALQEYRK | 16 |

EXAMPLE 3

A further set of experiments was conducted on an expanded number of peptides to further evaluate the effect of peptides according to the invention against HSV-1. Table 6 confirms that the peptides designated GIN 1p and GIN 7 had anti-HSV-1 properties, whereas the peptides designated GIN 32, 34 and 41 also had efficacy. The efficacy of these peptides is surprising given that the majority of peptides tested had little or no activity.

FIG. 7 compares and illustrates the effect of peptides GIN 7, GIN 32, GIN 34, and GIN 1p on HSV1 infectivity.

TABLE 6

| Peptide Code | SEQ ID No. | Nucleic acid SEQ ID No. | Sequence | IC$_{50}$ (μM) |
|---|---|---|---|---|
| 7 | SEQ ID No. 3 | SEQ ID No. 12 | WRKWRKRWWWRKWRKRWW | 3.5 |
| 34 | SEQ ID No. 5 | SEQ ID No. 14 | WRKWRKRWWLRKLRKRLL | 6 |
| 32 | SEQ ID No. 4 | SEQ ID No. 13 | WRKWRKRWRKWRKR | 10 |
| 41 | SEQ ID No. 6 | SEQ ID No. 15 | YRKYRKRYYYRKYRKRYY | 16 |
| 1p | SEQ ID No. 2 | SEQ ID No. 11 | LRKLRKRLLLRKLRKRLL | 17 |
| activity low: | | | | |
| 4 | SEQ ID No. 7 | SEQ ID No. 16 | LRKLRKRLLLRKLRK | 29.5 |
| 22 | SEQ ID No. 19 | NA | DWLKAFYDKVAEKLKEAF | 36 |
| 11 | SEQ ID No. 20 | NA | QSTEELRVRLASHLRKLRKRLL | 36.5 |
| 29 | SEQ ID No. 21 | NA | HMLDVMQDHFSRASSIIDEL | 38.5 |
| 10 | SEQ ID No. 22 | NA | RLLRLLRLLRLLRLLRLL | 39 |
| 44 | SEQ ID No. 23 | NA | LRQLRQRLLLRQLRQRLL | 40 |
| 2 | SEQ ID No. 24 | NA | LRKRLLLRKLRKRLL | >40 |
| 5 | SEQ ID No. 25 | NA | LRKLRKRLLLRK | >40 |
| 6 | SEQ ID No. 26 | NA | ERKERKREEERKERKREE | >40 |
| 12 | SEQ ID No. 27 | NA | LRKLRKRLLR DADDLQKRLA | >40 |
| 13 | SEQ ID No. 28 | NA | RDADDLQKR RDADDLQKR | >40 |
| 14 | SEQ ID No. 29 | NA | GERLRARMEGERLRARME | >40 |
| 15 | SEQ ID No. 30 | NA | RLRARMEEMRLRARMEEM | >40 |
| No activity: | | | | |
| apoE 141-149 | SEQ ID No. 1 | SEQ ID No. 10 | LRKLRKRLL | NA |
| 3 | SEQ ID No. 31 | NA | RLLLRKLRKRLL | NA |
| 6 | SEQ ID No. 32 | NA | ERKERKREEERKERKREE | NA |
| 17 | SEQ ID No. 33 | NA | RALVDTLKFVTQAEGAK | NA |
| 18 | SEQ ID No. 34 | NA | PYLDDFQKKWQEEMELYRQKVE | NA |
| 19 | SEQ ID No. 35 | NA | PLGEEMRDRARAHVDALRTHLA | NA |
| 20 | SEQ ID No. 36 | NA | PYSDELRQRLAARLEALKENGG | NA |
| 21 | SEQ ID No. 37 | NA | ARLAEYHAKATEHLSTLSEKAK | NA |
| 23 | SEQ ID No. 38 | NA | PVLDEFREKLNEELEALKQKMK | NA |
| 24 | SEQ ID No. 39 | NA | VTDYGKDLMEKVKSPELQ | NA |
| 25 | SEQ ID No. 40 | NA | VTDYGKDLMEKVKEWLNS | NA |
| 26 | SEQ ID No. 41 | NA | NFHAMFQPFLEMIHEAQQ | NA |
| 27 | SEQ ID No. 42 | NA | CKNKEKKCCKNKEKKC | NA |
| 28 | SEQ ID No. 43 | NA | LRKEKKRLLLRKEKKRLL | NA |
| 30 | SEQ ID No. 44 | NA | LQVAERLTRKYNELLKSYQ | NA |
| 31 | SEQ ID No. 45 | NA | KFMETVAEKALQEYRK | NA |
| 39 | SEQ ID No. 46 | NA | ARKARKRAAAARKARKRAA | NA |
| 40 | SEQ ID No. 47 | NA | MRKMRKRMMMRKMRKRMM | NA |
| 42 | SEQ ID No. 48 | NA | LRWLRWRLLLRWLRWRLL | NA |
| 45 | SEQ ID No. 49 | NA | LWKLWKWLLLWKLWKWLL | NA |
| 46 | SEQ ID No. 50 | NA | LYKLYKYLLLYKLYKYLL | NA |
| 47 | SEQ ID No. 51 | NA | LQKLQKQLLLQKLQKQLL | NA |

EXAMPLE 4

Similar experiments to those described in Example 2 were conducted to test the efficacy of the peptides according to the invention against HIV infection.

The glioma cell line NP2 over-expressing both CD4 and the appropriate co-receptor (CCR5 or CXCR4) were maintained in DMEM supplemented with 10% FCS. $2\times10^4$ cells were plated per well of a 48-well plate 24 h prior to infection and grown at 37 C. The cells were then washed, and incubated in DMEM/FCS containing peptide concentrations ranging from 0.1 to 10 micromolar, at 37 C for 30 minutes. 200 focus-forming units of HIV-1 stocks were then added to each well, and the cells incubated at 37 C for a further 2 hours. The cells were then washed twice in PBS and fresh medium replaced. After 3 day's growth the cells were fixed in cold methanol:acetone, and stained in situ for expression of HIV-1 p24 using a monoclonal anti-p24 followed by a secondary anti-mouse beta-galactosidase conjugate. Expression was visualised by X-Gal staining and infectious foci enumerated by light-microscopy.

It was found that peptides according to the invention had similar efficacy against HSV-1 and HIV.

FIG. 8 illustrates the anti-HIV action of peptide GIN 7 against HIV isolate SF162, grown in NP-2 glioma cells over-expressing CCR5 co-receptors.

Similar data was generated for other HIV strains, and in other host cells types. Notably GIN 1p (apoEdp) had no detectable anti-HIV activity in the one combination of HIV strain and cell type against which this peptide was tested, and at the concentrations used here (up to 10 μM). This would suggest the W substituted peptides according to the present invention are more potent against HIV than GIN 1p (apo $E_{141-149}$ dp).

EXAMPLE 5

Further experiments were conducted to test the efficacy of peptides according to the present invention against HSV1.

5.1 Methods

The methods employed were as described in Examples 1-4 expect peptides were prepared as 400 μM stocks in phosphate buffered saline (PBS).

5.2 Results

5.2.1 Effect of Complete Substitution of Leucine

Experiments were conducted to investigate the effect of full substitution of L residues in the apoE$_{141-149}$ tandem repeat with a single amino acid. Table 7 illustrates that peptides according to the present invention have efficacy for inhibiting the growth of HSV1 (i.e. W, R or K substitution). The peptides according to the first aspect of the invention surprisingly have more efficacy than the apoE tandom repeat (GIN 1/MU 10).

It is interesting to note that substitution with M, Y, F, I, Q, H or N had some efficacy (comparable with the apoE tandem repeat) and as such further substitutions according to the invention may comprise these amino acids.

Substitutions with E, A, D, S, V, T, G or P resulted in antiviral activity being abolished.

Although the inventors do not wish to be bound by any hypothesis they have noted that substitution with amino acids with small side chains tends to abolish antiviral activity whereas as amino acids with larger side chains maintain the antiviral effects. However substitution of L with amino acids as defined by the first aspect of the invention confers surprising antiviral activity.

TABLE 7

| Peptide Code | SEQ ID No. | Sequence | HSV1 IC$_{50}$ (μM) |
|---|---|---|---|
| MU 1 (GIN 6) | 67 | ERKERKREEERKERKREE | NA |
| MU 2 (GIN 39) | 68 | ARKARKRAAARKARKRAA | NA |
| MU 3 | 69 | DRKDRKRDDDRKDRKRDD | NA |
| MU 4 (GIN 7) | 3 | WRKWRKRWWWRKWRKRWW | 3.5 |
| MU 5 (GIN 40) | 70 | MRKMRKRMMMRKMRKRMM | >30 |
| MU 6 (GIN 41) | 6 | YRKYRKRYYYRKYRKRYY | >30 |
| MU 7 | 71 | FRKFRKRFFFRKFRKRFF | >30 |
| MU 8 | 72 | IRKIRKRIIIRKIRKRII | >30 |
| MU 9 | 73 | QRKQRKRQQQRKQRKRQQ | >30 |
| MU 10 (GIN 1p) | 2 | LRKLRKRLLLRKLRKRLL | 30 |
| MU 10 (GIN 1) | 2 | LRKLRKRLLLRKLRKRLL (no N/C protect) | 16.5 |
| MU 11 | 74 | NRKNRKRNNNRKNRKRNN | 27.5 |
| MU 13 | 75 | SRKSRKRSSSRKSRKRSS | NA |
| MU 14 | 76 | VRKVRKRVVVRKVRKRVV | NA |
| MU 15 | 77 | TRKTRKRTTTRKTRKRTT | NA |
| MU 16 | 64 | RRKRRKRRRRRKRRKRRR | 7.5 |
| MU 17 | 78 | GRKGRKRGGGRKGRKRGG | NA |
| MU 18 | 65 | KRKKRKRKKKRKKRKRKK | 7.5 |
| MU 19 | 79 | HRKHRKRHHHRKHRKRHH | NA |
| MU 20 | 80 | PRKPRKRPPPRKPRKRPP | NA |

5.2.2 Testing of Further apoE Derived Peptides.

The inventor constructed an expanded library of peptides to evaluate what apoE peptide derivatives may have antiviral activity.

Table 8 illustrates that a number of peptides, which were based on SEQ ID No. 2 but fall outside the definition of peptides according to the first aspect of the invention, had no or poor antiviral activity (e.g. MU 24-46). It is interesting to note that MU 43 and MU 44 correspond to tandem repeats of the murine and bovine equivalents to $apoE_{141-149}$ respectively whereas MU 46 corresponds to $apoE_{141-149}$ (SEQ ID No. 1).

The data presented in Table 8 for MU 58-117 demonstrate that each of these peptides, which are peptides according to the present invention have good antiviral activity which is surprisingly superior to that of $apoE_{141-149}$ dp (SEQ ID No. 2)

TABLE 8

| Peptide Code | SEQ ID No. | Sequence | HSV1 IC$_{50}$ (μM) |
|---|---|---|---|
| MU 24 | 81 | LLRKRLKRLLLRKRLKRL | 40 |
| MU 38 | 82 | LRRLRRRLLLRRLRRRLL | >30 |
| MU 39 | 83 | LKKLKKKLLLKKLKKKLL | 30 |
| MU 40 | 84 | LHHLHHHLLLHHLHHHLL | NA |
| MU 41 | 85 | LDDLDDDLLLDDLDDDLL | NA |
| MU 42 | 86 | LEELEEELLLEELEEELL | NA |
| MU 43 | 87 | MRKLRKRLMMRKLRKRLM | NA |
| MU 44 | 88 | LRKLPKRLLLRKLPKRLL | >30 |
| MU 45 | 89 | WRKWRKRWW | NA |
| MU 46 | 1 | LRKLRKRLL | NA |
| MU 58 | 52 | WRKWRKRWWWRKWRKRWW | 4.25 |
| MU 59 | 53 | WRKWRKRWRKWRKRW | 9.75 |
| MU 60 | 54 | WRKWRKRWWFRKWRKRWW | 4 |
| MU 61 | 55 | WRKWRKRFFWRKWRKRFF | 4.75 |
| MU 68 | 56 | WRKCRKRCWWRKCRKRCW | 4.25 |
| MU 83 | 66 | WRKWRKRWWWRWRKWRKRWWR | 2.5 |
| MU 111 | 57 | LRKLRKRLLWRKWRKRWW | 12.5 |
| MU 112 | 58 | LRKLRKRLLLRKLRKRWW | >20 |
| MU 113 | 59 | LRKLRKRLLWRKWRKRLL | 18.5 |
| MU 114 | 60 | WVRKWRKRLLLRKLRKRLL | 16 |
| MU 115 | 61 | WVRKLRKRLLLRKLRKRLL | 17.5 |
| MU 116 | 62 | WRKWRKFFFRKWRKRWW | 3.3 |
| MU 117 | 63 | WRKWRKRWWFRKFRKRFF | 3.3 |

EXAMPLE 6

Further experiments were conducted to test the efficacy of peptides according to the present invention against HSV2.

6.1 Methods

Plaque assays were performed. The methodology was as described in previous Examples for HSV1 plaque assays (including usage of Vero cells) except HSV2 clinical isolates (provided by Prof. Anthony Hart of Liverpool University) were employed instead.

6.2 Results

A number of peptides that were found to have efficacy against HSV1 were also tested against HSV2. Table 9 illustrates that peptides according to the present invention were effective against both HSV1 and HSV2. This illustrates that the peptides will have broad spectrum activity against viruses.

TABLE 9

| Peptide code | SEQ ID No. | Sequence | HSV2 IC$_{50}$ (μM) |
|---|---|---|---|
| GIN 34 | 5 | WRKWRKRWWLRKLRKRLL | <3.3 |
| GIN 32 | 4 | WRKWRKRWRKWRKR | 6.25 |
| MU 4 (GIN 7) | 3 | WRKWRKRWWWRKWRKRWW | <3.3 |
| MU 59 | 53 | WRKWRKRWRKWRKRW | 10 |
| MU 83 | 66 | WRKWRKRWWWRWRKWRKRWWR | <3.3 |
| MU 111 | 57 | LRKLRKRLLWRKWRKRWW | 6.5 |
| MU 112 | 58 | LRKLRKRLLLRKLRKRWW | 16 |
| MU 113 | 59 | LRKLRKRLLWRKWRKRLL | 11.75 |
| MU 114 | 60 | WRKWRKRLLLRKLRKRLL | 9 |

EXAMPLE 7

Further experiments were conducted to test the efficacy of peptides according to the present invention against Human Immunodeficiency Virus (HIV). The effect of a peptide according to the present invention was tested against a different HIV strain to that tested in Example 4.

7.1 Methods

Peptides (prepared as described previously) were diluted in 50 μl aliquots and mixed with T-cells (C8166) at 40,000 cells per well. Next HIV-1 111B was added at a multiplicity of infection (MOI) of 0.01, and the mixture incubated for 5 days at 37° C. Syncytia formation was assessed visually using an inverting microscope, and viral gp120 levels in supernatants assessed by a gp120 ELISA using GNA for antigen capture. 96-well plates coated with 50 ul GNA (Galanthus nivalis) were washed, then treated with 100 μl RPMI (10% foetal calf serum) and left for one hour. After further washing, 25 μl test sample supernatants were added to wells, along with dilutions of infected control samples. After lysis by 3 hr treatment with 0.5% Empigen (detergent used to lyse virus) to all wells, and washing, 50 μl of human anti-HIV sera was added, and plates incubated overnight. After further washing, 50 μl of a 1000× dilution of anti-human Ig peroxidase conjugate was added, and plates incubated at 37° C. for 90 min. After a final wash, 50 ul peroxidase substrate was added to each well, and plates incubated for 10-30 min. Reaction was stopped with 25 μl 2M $H_2SO_4$, and A450 measured.

7.2 Results

Further tests were conducted to support the data presented in Example 4 illustrating that peptides according to the present invention were effective against HIV as well as both HSV1 and HSV2.

GIN 32 (SEQ ID No. 4) had an IC$_{50}$ of 7.5 μM for inhibiting HIV-1 growth. The efficacy of this was similar in HSV 1, HSV2 and HIV. This confirms that peptides according to the present invention have broad antiviral effects.

The invention claimed is:

1. An isolated and purified antiviral polypeptide comprising between 14 and 18 amino acids of the apoE$_{141-149}$ tandem repeat set forth in SEQ ID No 2, wherein said polypeptide comprises one or more amino acid substitutions of tryptophan (W) for leucine (L).

2. The polypeptide of claim 1 wherein at least two W substitutions are made.

3. The polypeptide of claim 1 wherein at least one further leucine amino acid is replaced with Phenylalanine (F) or is deleted.

4. The polypeptide of claim 1 with the amino acid sequence: WRKWRKRWWWRKWRKRWW (SEQ ID No. 3); WRKWRKRWRKWRKR (SEQ ID No. 4); WRKWRKRWWLRKLRKRLL (SEQ ID No. 5); or WRKWRKRWFFRKWRKRFF (SEQ ID No. 55).

5. The polypeptide of claim 1 wherein an amino acid is added to the N terminal, C terminal and/or between the ninth and tenth amino acids of SEQ ID No.2.

6. The polypeptide of claim 5 comprising WRKWRKRWWRWRKWRKRWWR (SEQ ID No. 66).

7. An isolated and purified antiviral polypeptide comprising YRKYRKRYYYRKYRKRYY (SEQ ID No. 6).

8. An isolated and purified antiviral polypeptide comprising LRKLRKRLLLRKLRK (SEQ ID No. 7).

9. An isolated and purified antiviral polypeptide comprising LRKLRKRLRKLRKR (SEQ ID No. 8).

10. An isolated and purified antiviral polypeptide comprising LRKLRKLRKLRKLRK (SEQ ID No. 9).

11. A composition, comprising the polypeptide of claim 1.

12. A method of inhibiting viral replication, comprising administering to a subject in need of such treatment a therapeutically effective amount of the polypeptide of claim 1.

13. The method of claim 12, wherein the polypeptide is the polypeptide of claim 2.

14. The method of claim 12, wherein the polypeptide is the polypeptide of claim 3.

15. The method of claim 12, wherein the polypeptide is the polypeptide of claim 4.

16. The method of claim 12, wherein the polypeptide is the polypeptide of claim 5.

17. The method of claim 12, wherein the polypeptide is the polypeptide of claim 6.

18. The method of claim 12, wherein the polypeptide is an isolated and purified antiviral polypeptide comprising YRKYRKRYYYRKYRKRYY (SEQ ID No. 6).

19. The method of claim 12, wherein the polypeptide is an isolated and purified antiviral polypeptide comprising LRKLRKRLLLRKLRK (SEQ ID No. 7).

20. The method of claim 12, wherein the polypeptide is an isolated and purified antiviral polypeptide comprising LRKLRKRLRKLRKR (SEQ ID No. 8).

21. The method of claim 12, wherein the polypeptide is an isolated and purified antiviral polypeptide comprising LRKLRKLRKLRKLRK (SEQ ID No. 9).

22. An isolated and purified antiviral polypeptide derived from the apoE141-149 tandem repeat set forth in SEQ ID No. 2 selected from the group consisting of:

| | |
|---|---|
| WRKWRKRWWRKWRKRWW, | (SEQ ID No. 52) |
| WRKWRKRWRKWRKRW, | (SEQ ID No. 53) |
| WRKWRKRWWFRKWRKRWW, | (SEQ ID No. 54) |
| WRKCRKRCWWRKCRKRCW, | (SEQ ID No. 56) |

| | |
|---|---|
| LRKLRKRLLWRKWRKRWW, | (SEQ ID No. 57) |
| LRKLRKRLLLRKLRKRWW, | (SEQ ID No. 58) |
| LRKLRKRLLWRKWRKRLL, | (SEQ ID No. 59) |
| WRKWRKRLLLRKLRKRLL, | (SEQ ID No. 60) |
| WRKLRKRLLLRKLRKRLL, | (SEQ ID No. 61) |
| WRKWRKFFFRKWRKRWW, | (SEQ ID No. 62) |
| WRKWRKRWWFRKFRKRFF, | (SEQ ID No. 63) |
| RRKRRKRRRRKRRKRRR, | (SEQ ID No. 64) |
| and | |
| KRKKRKRKKKRKKRKRKK | (SEQ ID No. 65). |

23. A method of inhibiting viral replication, comprising administering to a subject in need of such treatment a therapeutically effective amount of the polypeptide of claim 22.

* * * * *

SEQUENCE LISTING

<160> NUMBER OF SEQ IDS NOS: 89

<210> SEQ ID NO 1
<211> LENGTH: 9
<212> TYPE: PRT
<213> ORGANISM: Homo sapiens

<400> SEQUENCE: 1

Leu Arg Lys Leu Arg Lys Arg Leu Leu
1               5

<210> SEQ ID NO 2
<211> LENGTH: 18
<212> TYPE: PRT
<213> ORGANISM: Homo sapiens

<400> SEQUENCE: 2

Leu Arg Lys Leu Arg Lys Arg Leu Leu Leu Arg Lys Leu Arg Lys Arg
1               5                   10                  15

Leu Leu

<210> SEQ ID NO 3
<211> LENGTH: 18
<212> TYPE: PRT
<213> ORGANISM: Homo sapiens

<400> SEQUENCE: 3

Trp Arg Lys Trp Arg Lys Arg Trp Trp Trp Arg Lys Trp Arg Lys Arg
1               5                   10                  15

Trp Trp

<210> SEQ ID NO 4
<211> LENGTH: 14
<212> TYPE: PRT
<213> ORGANISM: Homo sapiens

<400> SEQUENCE: 4

Trp Arg Lys Trp Arg Lys Arg Trp Arg Lys Trp Arg Lys Arg
1               5                   10

<210> SEQ ID NO 5
<211> LENGTH: 18
<212> TYPE: PRT
<213> ORGANISM: Homo sapiens

<400> SEQUENCE: 5

Trp Arg Lys Trp Arg Lys Arg Trp Trp Leu Arg Lys Leu Arg Lys Arg
1               5                   10                  15

Leu Leu

<210> SEQ ID NO 6
<211> LENGTH: 18
<212> TYPE: PRT
<213> ORGANISM: Homo sapiens

<400> SEQUENCE: 6

Tyr Arg Lys Tyr Arg Lys Arg Tyr Tyr Tyr Arg Lys Tyr Arg Lys Arg
1               5                   10                  15

Tyr Tyr

```
<210> SEQ ID NO 7
<211> LENGTH: 15
<212> TYPE: PRT
<213> ORGANISM: Homo sapiens

<400> SEQUENCE: 7

Leu Arg Lys Leu Arg Lys Arg Leu Leu Arg Lys Leu Arg Lys
1               5                   10                  15

<210> SEQ ID NO 8
<211> LENGTH: 14
<212> TYPE: PRT
<213> ORGANISM: Homo sapiens

<400> SEQUENCE: 8

Leu Arg Lys Leu Arg Lys Arg Leu Arg Lys Leu Arg Lys Arg
1               5                   10

<210> SEQ ID NO 9
<211> LENGTH: 18
<212> TYPE: PRT
<213> ORGANISM: Homo sapiens

<400> SEQUENCE: 9

Leu Arg Lys Leu Arg Lys Leu Arg Lys Leu Arg Lys Leu Arg Lys Leu
1               5                   10                  15

Arg Lys

<210> SEQ ID NO 10
<211> LENGTH: 27
<212> TYPE: DNA
<213> ORGANISM: Homo sapiens

<400> SEQUENCE: 10
cttcgtaaac ttcgtaaacg tcttctt                                    27

<210> SEQ ID NO 11
<211> LENGTH: 54
<212> TYPE: DNA
<213> ORGANISM: Homo sapiens

<400> SEQUENCE: 11
cttcgtaaac ttcgtaaacg tcttcttctt cgtaaacttc gtaaacgtct tctt      54

<210> SEQ ID NO 12
<211> LENGTH: 54
<212> TYPE: DNA
<213> ORGANISM: Homo sapiens

<400> SEQUENCE: 12
tggcgtaaat ggcgtaaacg ttggtggtgg cgtaaatggc gtaaacgttg gtgg      54

<210> SEQ ID NO 13
<211> LENGTH: 42
<212> TYPE: DNA
<213> ORGANISM: Homo sapiens

<400> SEQUENCE: 13
tggcgtaaat ggcgtaaacg ttggcgtaaa tggcgtaaac gt                   42

<210> SEQ ID NO 14
<211> LENGTH: 54
<212> TYPE: DNA
```

```
<400> SEQUENCE: 14
tggcgtaaat ggcgtaaacg ttggtggctt cgtaaacttc gtaaacgtct tctt         54

<210> SEQ ID NO 15
<211> LENGTH: 54
<212> TYPE: DNA
<213> ORGANISM: Homo sapiens

<400> SEQUENCE: 15
tatcgtaaat atcgtaaacg ttattattat cgtaaatatc gtaaacgtta ttat         54

<210> SEQ ID NO 16
<211> LENGTH: 45
<212> TYPE: DNA
<213> ORGANISM: Homo sapiens

<400> SEQUENCE: 16
cttcgtaaac ttcgtaaacg tcttcttctt cgtaaacttc gtaaa                   45

<210> SEQ ID NO 17
<211> LENGTH: 42
<212> TYPE: DNA
<213> ORGANISM: Homo sapiens

<400> SEQUENCE: 17
cttcgtaaac ttcgtaaacg tcttcgtaaa cttcgtaaac gt                      42

<210> SEQ ID NO 18
<211> LENGTH: 54
<212> TYPE: DNA
<213> ORGANISM: Homo sapiens

<400> SEQUENCE: 18
cttcgtaaac ttcgtaaact tcgtaaactt cgtaaacttc gtaaacttcg taaa         54

<210> SEQ ID NO 19
<211> LENGTH: 18
<212> TYPE: PRT
<213> ORGANISM: Homo sapiens

<400> SEQUENCE: 19

Asp Trp Leu Lys Ala Phe Tyr Asp Lys Val Ala Glu Lys Leu Lys Glu
1               5                   10                  15

Ala Phe

<210> SEQ ID NO 20
<211> LENGTH: 22
<212> TYPE: PRT
<213> ORGANISM: Homo sapiens

<400> SEQUENCE: 20

Gln Ser Thr Glu Glu Leu Arg Val Arg Leu Ala Ser His Leu Arg Lys
1               5                   10                  15

Leu Arg Lys Arg Leu Leu
            20

<210> SEQ ID NO 21
<211> LENGTH: 20
<212> TYPE: PRT
<213> ORGANISM: Homo sapiens
```

```
<400> SEQUENCE: 21

His Met Leu Asp Val Met Gln Asp His Phe Ser Arg Ala Ser Ser Ile
1               5                   10                  15

Ile Asp Glu Leu
            20

<210> SEQ ID NO 22
<211> LENGTH: 18
<212> TYPE: PRT
<213> ORGANISM: Homo sapiens

<400> SEQUENCE: 22

Arg Leu Leu Arg Leu Leu Arg Leu Leu Arg Leu Leu Arg Leu Leu Arg
1               5                   10                  15

Leu Leu

<210> SEQ ID NO 23
<211> LENGTH: 18
<212> TYPE: PRT
<213> ORGANISM: Homo sapiens

<400> SEQUENCE: 23

Leu Arg Gln Leu Arg Gln Arg Leu Leu Arg Gln Leu Arg Gln Arg
1               5                   10                  15

Leu Leu

<210> SEQ ID NO 24
<211> LENGTH: 15
<212> TYPE: PRT
<213> ORGANISM: Homo sapiens

<400> SEQUENCE: 24

Leu Arg Lys Arg Leu Leu Leu Arg Lys Leu Arg Lys Arg Leu Leu
1               5                   10                  15

<210> SEQ ID NO 25
<211> LENGTH: 12
<212> TYPE: PRT
<213> ORGANISM: Homo sapiens

<400> SEQUENCE: 25

Leu Arg Lys Leu Arg Lys Arg Leu Leu Leu Arg Lys
1               5                   10

<210> SEQ ID NO 26
<211> LENGTH: 18
<212> TYPE: PRT
<213> ORGANISM: Homo sapiens

<400> SEQUENCE: 26

Glu Arg Lys Glu Arg Lys Arg Glu Glu Glu Arg Lys Glu Arg Lys Arg
1               5                   10                  15

Glu Glu

<210> SEQ ID NO 27
<211> LENGTH: 20
<212> TYPE: PRT
<213> ORGANISM: Homo sapiens
```

```
<400> SEQUENCE: 27

Leu Arg Lys Leu Arg Lys Arg Leu Leu Arg Asp Ala Asp Asp Leu Gln
1               5                   10                  15

Lys Arg Leu Ala
            20

<210> SEQ ID NO 28
<211> LENGTH: 18
<212> TYPE: PRT
<213> ORGANISM: Homo sapiens

<400> SEQUENCE: 28

Arg Asp Ala Asp Asp Leu Gln Lys Arg Arg Asp Ala Asp Asp Leu Gln
1               5                   10                  15

Lys Arg

<210> SEQ ID NO 29
<211> LENGTH: 18
<212> TYPE: PRT
<213> ORGANISM: Homo sapiens

<400> SEQUENCE: 29

Gly Glu Arg Leu Arg Ala Arg Met Glu Gly Glu Arg Leu Arg Ala Arg
1               5                   10                  15

Met Glu

<210> SEQ ID NO 30
<211> LENGTH: 18
<212> TYPE: PRT
<213> ORGANISM: Homo sapiens

<400> SEQUENCE: 30

Arg Leu Arg Ala Arg Met Glu Glu Met Arg Leu Arg Ala Arg Met Glu
1               5                   10                  15

Glu Met

<210> SEQ ID NO 31
<211> LENGTH: 12
<212> TYPE: PRT
<213> ORGANISM: Homo sapiens

<400> SEQUENCE: 31

Arg Leu Leu Leu Arg Lys Leu Arg Lys Arg Leu Leu
1               5                   10

<210> SEQ ID NO 32
<211> LENGTH: 18
<212> TYPE: PRT
<213> ORGANISM: Homo sapiens

<400> SEQUENCE: 32

Glu Arg Lys Glu Arg Lys Arg Glu Glu Glu Arg Lys Glu Arg Lys Arg
1               5                   10                  15

Glu Glu

<210> SEQ ID NO 33
<211> LENGTH: 17
<212> TYPE: PRT
<213> ORGANISM: Homo sapiens
```

```
<400> SEQUENCE: 33

Arg Ala Leu Val Asp Thr Leu Lys Phe Val Thr Gln Ala Glu Gly Ala
1               5                   10                  15

Lys

<210> SEQ ID NO 34
<211> LENGTH: 22
<212> TYPE: PRT
<213> ORGANISM: Homo sapiens

<400> SEQUENCE: 34

Pro Tyr Leu Asp Asp Phe Gln Lys Lys Trp Gln Glu Glu Met Glu Leu
1               5                   10                  15

Tyr Arg Gln Lys Val Glu
            20

<210> SEQ ID NO 35
<211> LENGTH: 22
<212> TYPE: PRT
<213> ORGANISM: Homo sapiens

<400> SEQUENCE: 35

Pro Leu Gly Glu Glu Met Arg Asp Arg Ala Arg Ala His Val Asp Ala
1               5                   10                  15

Leu Arg Thr His Leu Ala
            20

<210> SEQ ID NO 36
<211> LENGTH: 22
<212> TYPE: PRT
<213> ORGANISM: Homo sapiens

<400> SEQUENCE: 36

Pro Tyr Ser Asp Glu Leu Arg Gln Arg Leu Ala Ala Arg Leu Glu Ala
1               5                   10                  15

Leu Lys Glu Asn Gly Gly
            20

<210> SEQ ID NO 37
<211> LENGTH: 22
<212> TYPE: PRT
<213> ORGANISM: Homo sapiens

<400> SEQUENCE: 37

Ala Arg Leu Ala Glu Tyr His Ala Lys Ala Thr Glu His Leu Ser Thr
1               5                   10                  15

Leu Ser Glu Lys Ala Lys
            20

<210> SEQ ID NO 38
<211> LENGTH: 22
<212> TYPE: PRT
<213> ORGANISM: Homo sapiens

<400> SEQUENCE: 38

Pro Val Leu Asp Glu Phe Arg Glu Lys Leu Asn Glu Glu Leu Glu Ala
1               5                   10                  15

Leu Lys Gln Lys Met Lys
            20
```

<210> SEQ ID NO 39
<211> LENGTH: 18
<212> TYPE: PRT
<213> ORGANISM: Homo sapiens

<400> SEQUENCE: 39

Val Thr Asp Tyr Gly Lys Asp Leu Met Glu Lys Val Lys Ser Pro Glu
1               5                   10                  15

Leu Gln

<210> SEQ ID NO 40
<211> LENGTH: 18
<212> TYPE: PRT
<213> ORGANISM: Homo sapiens

<400> SEQUENCE: 40

Val Thr Asp Tyr Gly Lys Asp Leu Met Glu Lys Val Lys Glu Trp Leu
1               5                   10                  15

Asn Ser

<210> SEQ ID NO 41
<211> LENGTH: 18
<212> TYPE: PRT
<213> ORGANISM: Homo sapiens

<400> SEQUENCE: 41

Asn Phe His Ala Met Phe Gln Pro Phe Leu Glu Met Ile His Glu Ala
1               5                   10                  15

Gln Gln

<210> SEQ ID NO 42
<211> LENGTH: 16
<212> TYPE: PRT
<213> ORGANISM: Homo sapiens

<400> SEQUENCE: 42

Cys Lys Asn Lys Glu Lys Lys Cys Cys Lys Asn Lys Glu Lys Lys Cys
1               5                   10                  15

<210> SEQ ID NO 43
<211> LENGTH: 18
<212> TYPE: PRT
<213> ORGANISM: Homo sapiens

<400> SEQUENCE: 43

Leu Arg Lys Glu Lys Lys Arg Leu Leu Arg Lys Glu Lys Lys Arg
1               5                   10                  15

Leu Leu

<210> SEQ ID NO 44
<211> LENGTH: 19
<212> TYPE: PRT
<213> ORGANISM: Homo sapiens

<400> SEQUENCE: 44

Leu Gln Val Ala Glu Arg Leu Thr Arg Lys Tyr Asn Glu Leu Leu Lys
1               5                   10                  15

Ser Tyr Gln

```
<210> SEQ ID NO 45
<211> LENGTH: 16
<212> TYPE: PRT
<213> ORGANISM: Homo sapiens

<400> SEQUENCE: 45

Lys Phe Met Glu Thr Val Ala Glu Lys Ala Leu Gln Glu Tyr Arg Lys
1               5                   10                  15

<210> SEQ ID NO 46
<211> LENGTH: 18
<212> TYPE: PRT
<213> ORGANISM: Homo sapiens

<400> SEQUENCE: 46

Ala Arg Lys Ala Arg Lys Arg Ala Ala Ala Arg Lys Ala Arg Lys Arg
1               5                   10                  15

Ala Ala

<210> SEQ ID NO 47
<211> LENGTH: 18
<212> TYPE: PRT
<213> ORGANISM: Homo sapiens

<400> SEQUENCE: 47

Met Arg Lys Met Arg Lys Arg Met Met Met Arg Lys Met Arg Lys Arg
1               5                   10                  15

Met Met

<210> SEQ ID NO 48
<211> LENGTH: 18
<212> TYPE: PRT
<213> ORGANISM: Homo sapiens

<400> SEQUENCE: 48

Leu Arg Trp Leu Arg Trp Arg Leu Leu Leu Arg Trp Leu Arg Trp Arg
1               5                   10                  15

Leu Leu

<210> SEQ ID NO 49
<211> LENGTH: 18
<212> TYPE: PRT
<213> ORGANISM: Homo sapiens

<400> SEQUENCE: 49

Leu Trp Lys Leu Trp Lys Trp Leu Leu Leu Trp Lys Leu Trp Lys Trp
1               5                   10                  15

Leu Leu

<210> SEQ ID NO 50
<211> LENGTH: 18
<212> TYPE: PRT
<213> ORGANISM: Homo sapiens

<400> SEQUENCE: 50

Leu Tyr Lys Leu Tyr Lys Tyr Leu Leu Leu Tyr Lys Leu Tyr Lys Tyr
1               5                   10                  15

Leu Leu
```

```
<210> SEQ ID NO 51
<211> LENGTH: 18
<212> TYPE: PRT
<213> ORGANISM: Homo sapiens

<400> SEQUENCE: 51

Leu Gln Lys Leu Gln Lys Gln Leu Leu Leu Gln Lys Leu Gln Lys Gln
1               5                   10                  15

Leu Leu

<210> SEQ ID NO 52
<211> LENGTH: 17
<212> TYPE: PRT
<213> ORGANISM: Homo sapiens

<400> SEQUENCE: 52

Trp Arg Lys Trp Arg Lys Arg Trp Trp Arg Lys Trp Arg Lys Arg Trp
1               5                   10                  15

Trp

<210> SEQ ID NO 53
<211> LENGTH: 15
<212> TYPE: PRT
<213> ORGANISM: Homo sapiens

<400> SEQUENCE: 53

Trp Arg Lys Trp Arg Lys Arg Trp Arg Lys Trp Arg Lys Arg Trp
1               5                   10                  15

<210> SEQ ID NO 54
<211> LENGTH: 18
<212> TYPE: PRT
<213> ORGANISM: Homo sapiens

<400> SEQUENCE: 54

Trp Arg Lys Trp Arg Lys Arg Trp Phe Arg Lys Trp Arg Lys Arg
1               5                   10                  15

Trp Trp

<210> SEQ ID NO 55
<211> LENGTH: 18
<212> TYPE: PRT
<213> ORGANISM: Homo sapiens

<400> SEQUENCE: 55

Trp Arg Lys Trp Arg Lys Arg Trp Phe Phe Arg Lys Trp Arg Lys Arg
1               5                   10                  15

Phe Phe

<210> SEQ ID NO 56
<211> LENGTH: 18
<212> TYPE: PRT
<213> ORGANISM: Homo sapiens

<400> SEQUENCE: 56

Trp Arg Lys Cys Arg Lys Arg Cys Trp Trp Arg Lys Cys Arg Lys Arg
1               5                   10                  15

Cys Trp
```

```
<210> SEQ ID NO 57
<211> LENGTH: 18
<212> TYPE: PRT
<213> ORGANISM: Homo sapiens

<400> SEQUENCE: 57

Leu Arg Lys Leu Arg Lys Arg Leu Leu Trp Arg Lys Trp Arg Lys Arg
1               5                   10                  15

Trp Trp

<210> SEQ ID NO 58
<211> LENGTH: 18
<212> TYPE: PRT
<213> ORGANISM: Homo sapiens

<400> SEQUENCE: 58

Leu Arg Lys Leu Arg Lys Arg Leu Leu Arg Lys Leu Arg Lys Arg
1               5                   10                  15

Trp Trp

<210> SEQ ID NO 59
<211> LENGTH: 18
<212> TYPE: PRT
<213> ORGANISM: Homo sapiens

<400> SEQUENCE: 59

Leu Arg Lys Leu Arg Lys Arg Leu Leu Trp Arg Lys Trp Arg Lys Arg
1               5                   10                  15

Leu Leu

<210> SEQ ID NO 60
<211> LENGTH: 18
<212> TYPE: PRT
<213> ORGANISM: Homo sapiens

<400> SEQUENCE: 60

Trp Arg Lys Trp Arg Lys Arg Leu Leu Leu Arg Lys Leu Arg Lys Arg
1               5                   10                  15

Leu Leu

<210> SEQ ID NO 61
<211> LENGTH: 18
<212> TYPE: PRT
<213> ORGANISM: Homo sapiens

<400> SEQUENCE: 61

Trp Arg Lys Leu Arg Lys Arg Leu Leu Leu Arg Lys Leu Arg Lys Arg
1               5                   10                  15

Leu Leu

<210> SEQ ID NO 62
<211> LENGTH: 17
<212> TYPE: PRT
<213> ORGANISM: Homo sapiens

<400> SEQUENCE: 62

Trp Arg Lys Trp Arg Lys Phe Phe Phe Arg Lys Trp Arg Lys Arg Trp
1               5                   10                  15

Trp
```

```
<210> SEQ ID NO 63
<211> LENGTH: 18
<212> TYPE: PRT
<213> ORGANISM: Homo sapiens

<400> SEQUENCE: 63

Trp Arg Lys Trp Arg Lys Arg Trp Trp Phe Arg Lys Phe Arg Lys Arg
1               5                   10                  15

Phe Phe

<210> SEQ ID NO 64
<211> LENGTH: 18
<212> TYPE: PRT
<213> ORGANISM: Homo sapiens

<400> SEQUENCE: 64

Arg Arg Lys Arg Arg Lys Arg Arg Arg Arg Lys Arg Arg Lys Arg
1               5                   10                  15

Arg Arg

<210> SEQ ID NO 65
<211> LENGTH: 18
<212> TYPE: PRT
<213> ORGANISM: Homo sapiens

<400> SEQUENCE: 65

Lys Arg Lys Lys Arg Lys Arg Lys Lys Lys Arg Lys Lys Arg Lys Arg
1               5                   10                  15

Lys Lys

<210> SEQ ID NO 66
<211> LENGTH: 20
<212> TYPE: PRT
<213> ORGANISM: Homo sapiens

<400> SEQUENCE: 66

Trp Arg Lys Trp Arg Lys Arg Trp Trp Arg Trp Arg Lys Trp Arg Lys
1               5                   10                  15

Arg Trp Trp Arg
            20

<210> SEQ ID NO 67
<211> LENGTH: 18
<212> TYPE: PRT
<213> ORGANISM: Homo sapiens

<400> SEQUENCE: 67

Glu Arg Lys Glu Arg Lys Arg Glu Glu Glu Arg Lys Glu Arg Lys Arg
1               5                   10                  15

Glu Glu

<210> SEQ ID NO 68
<211> LENGTH: 18
<212> TYPE: PRT
<213> ORGANISM: Homo sapiens

<400> SEQUENCE: 68

Ala Arg Lys Ala Arg Lys Arg Ala Ala Ala Arg Lys Ala Arg Lys Arg
1               5                   10                  15

Ala Ala
```

```
<210> SEQ ID NO 69
<211> LENGTH: 18
<212> TYPE: PRT
<213> ORGANISM: Homo sapiens

<400> SEQUENCE: 69

Asp Arg Lys Asp Arg Lys Arg Asp Asp Asp Arg Lys Asp Arg Lys Arg
1               5                   10                  15
Asp Asp

<210> SEQ ID NO 70
<211> LENGTH: 18
<212> TYPE: PRT
<213> ORGANISM: Homo sapiens

<400> SEQUENCE: 70

Met Arg Lys Met Arg Lys Arg Met Met Met Arg Lys Met Arg Lys Arg
1               5                   10                  15
Met Met

<210> SEQ ID NO 71
<211> LENGTH: 18
<212> TYPE: PRT
<213> ORGANISM: Homo sapiens

<400> SEQUENCE: 71

Phe Arg Lys Phe Arg Lys Arg Phe Phe Phe Arg Lys Phe Arg Lys Arg
1               5                   10                  15
Phe Phe

<210> SEQ ID NO 72
<211> LENGTH: 18
<212> TYPE: PRT
<213> ORGANISM: Homo sapiens

<400> SEQUENCE: 72

Ile Arg Lys Ile Arg Lys Arg Ile Ile Ile Arg Lys Ile Arg Lys Arg
1               5                   10                  15
Ile Ile

<210> SEQ ID NO 73
<211> LENGTH: 18
<212> TYPE: PRT
<213> ORGANISM: Homo sapiens

<400> SEQUENCE: 73

Gln Arg Lys Gln Arg Lys Arg Gln Gln Gln Arg Lys Gln Arg Lys Arg
1               5                   10                  15
Gln Gln

<210> SEQ ID NO 74
<211> LENGTH: 18
<212> TYPE: PRT
<213> ORGANISM: Homo sapiens

<400> SEQUENCE: 74

Asn Arg Lys Asn Arg Lys Arg Asn Asn Asn Arg Lys Asn Arg Lys Arg
1               5                   10                  15
Asn Asn
```

```
<210> SEQ ID NO 75
<211> LENGTH: 18
<212> TYPE: PRT
<213> ORGANISM: Homo sapiens

<400> SEQUENCE: 75

Ser Arg Lys Ser Arg Lys Arg Ser Ser Arg Lys Ser Arg Lys Arg
1               5                   10                  15

Ser Ser

<210> SEQ ID NO 76
<211> LENGTH: 18
<212> TYPE: PRT
<213> ORGANISM: Homo sapiens

<400> SEQUENCE: 76

Val Arg Lys Val Arg Lys Arg Val Val Arg Lys Val Arg Lys Arg
1               5                   10                  15

Val Val

<210> SEQ ID NO 77
<211> LENGTH: 18
<212> TYPE: PRT
<213> ORGANISM: Homo sapiens

<400> SEQUENCE: 77

Thr Arg Lys Thr Arg Lys Arg Thr Thr Arg Lys Thr Arg Lys Arg
1               5                   10                  15

Thr Thr

<210> SEQ ID NO 78
<211> LENGTH: 18
<212> TYPE: PRT
<213> ORGANISM: Homo sapiens

<400> SEQUENCE: 78

Gly Arg Lys Gly Arg Lys Arg Gly Gly Arg Lys Gly Arg Lys Arg
1               5                   10                  15

Gly Gly

<210> SEQ ID NO 79
<211> LENGTH: 18
<212> TYPE: PRT
<213> ORGANISM: Homo sapiens

<400> SEQUENCE: 79

His Arg Lys His Arg Lys Arg His His Arg Lys His Arg Lys Arg
1               5                   10                  15

His His

<210> SEQ ID NO 80
<211> LENGTH: 18
<212> TYPE: PRT
<213> ORGANISM: Homo sapiens

<400> SEQUENCE: 80

Pro Arg Lys Pro Arg Lys Arg Pro Pro Arg Lys Pro Arg Lys Arg
1               5                   10                  15

Pro Pro
```

```
<210> SEQ ID NO 81
<211> LENGTH: 18
<212> TYPE: PRT
<213> ORGANISM: Homo sapiens

<400> SEQUENCE: 81

Leu Leu Arg Lys Arg Leu Lys Arg Leu Leu Arg Lys Arg Leu Lys
1               5                   10                  15

Arg Leu

<210> SEQ ID NO 82
<211> LENGTH: 18
<212> TYPE: PRT
<213> ORGANISM: Homo sapiens

<400> SEQUENCE: 82

Leu Arg Arg Leu Arg Arg Arg Leu Leu Arg Arg Leu Arg Arg Arg
1               5                   10                  15

Leu Leu

<210> SEQ ID NO 83
<211> LENGTH: 18
<212> TYPE: PRT
<213> ORGANISM: Homo sapiens

<400> SEQUENCE: 83

Leu Lys Lys Leu Lys Lys Lys Leu Leu Leu Lys Lys Leu Lys Lys Lys
1               5                   10                  15

Leu Leu

<210> SEQ ID NO 84
<211> LENGTH: 18
<212> TYPE: PRT
<213> ORGANISM: Homo sapiens

<400> SEQUENCE: 84

Leu His His Leu His His His Leu Leu Leu His His Leu His His His
1               5                   10                  15

Leu Leu

<210> SEQ ID NO 85
<211> LENGTH: 18
<212> TYPE: PRT
<213> ORGANISM: Homo sapiens

<400> SEQUENCE: 85

Leu Asp Asp Leu Asp Asp Asp Leu Leu Leu Asp Asp Leu Asp Asp Asp
1               5                   10                  15

Leu Leu

<210> SEQ ID NO 86
<211> LENGTH: 18
<212> TYPE: PRT
<213> ORGANISM: Homo sapiens

<400> SEQUENCE: 86

Leu Glu Glu Leu Glu Glu Glu Leu Leu Leu Glu Glu Leu Glu Glu Glu
1               5                   10                  15

Leu Leu
```

-continued

```
<210> SEQ ID NO 87
<211> LENGTH: 18
<212> TYPE: PRT
<213> ORGANISM: Homo sapiens

<400> SEQUENCE: 87

Met Arg Lys Leu Arg Lys Arg Leu Met Met Arg Lys Leu Arg Lys Arg
1               5                   10                  15

Leu Met

<210> SEQ ID NO 88
<211> LENGTH: 18
<212> TYPE: PRT
<213> ORGANISM: Homo sapiens

<400> SEQUENCE: 88

Leu Arg Lys Leu Pro Lys Arg Leu Leu Leu Arg Lys Leu Pro Lys Arg
1               5                   10                  15

Leu Leu

<210> SEQ ID NO 89
<211> LENGTH: 9
<212> TYPE: PRT
<213> ORGANISM: Homo sapiens

<400> SEQUENCE: 89

Trp Arg Lys Trp Arg Lys Arg Trp Trp
1               5
```